United States Patent
Boyce et al.

(10) Patent No.: US 7,608,723 B2
(45) Date of Patent: Oct. 27, 2009

(54) INDOLE AND BENZIMIDAZOLE DERIVATIVES

(75) Inventors: Rustum S. Boyce, Singapore (CN); Yi Xia, Palo Alto, CA (US); Hongyan Guo, Foster City, CA (US); Kris G. Mendenhull, Concord, CA (US); Annette O. Walter, Mill Valley, CA (US); Weibo Wang, Moraga, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 378 days.

(21) Appl. No.: 11/251,440

(22) Filed: Oct. 14, 2005

(65) Prior Publication Data

US 2006/0084687 A1 Apr. 20, 2006

Related U.S. Application Data

(60) Provisional application No. 60/620,385, filed on Oct. 19, 2004.

(51) Int. Cl.
*C07D 209/10* (2006.01)
*C07D 235/14* (2006.01)
*A61K 31/33* (2006.01)

(52) U.S. Cl. .................. 548/309.7; 548/507; 514/394; 514/415

(58) Field of Classification Search .......... 548/507, 548/309.7
See application file for complete search history.

(56) References Cited

U.S. PATENT DOCUMENTS

| 6,271,241 | B1 * | 8/2001 | DeSimone et al. ........ 514/303 |
|---|---|---|---|
| 6,545,004 | B1 | 4/2003 | Finer et al. |
| 6,562,831 | B1 | 5/2003 | Finer et al. |
| 6,630,479 | B1 | 10/2003 | Finer et al. |
| 2002/0151550 | A1 * | 10/2002 | DeSimone et al. ........ 514/248 |

FOREIGN PATENT DOCUMENTS

| WO | WO 00/59887 | 10/2000 |
|---|---|---|
| WO | WO 01/30768 A1 | 5/2001 |
| WO | WO 02/10140 A2 | 2/2002 |
| WO | WO 02/28839 A1 | 4/2002 |
| WO | WO 02/46168 A1 | 6/2002 |
| WO | WO 02/056880 A1 | 7/2002 |
| WO | WO 02/057244 A1 | 7/2002 |
| WO | WO 03/039460 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/059289 A2 | 7/2003 |
| WO | WO 03/070701 A2 | 8/2003 |
| WO | WO 03/079973 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/186417 A1 | 12/2003 |
| WO | WO 2004/004652 A2 | 1/2004 |
| WO | WO 2004/006865 A2 | 1/2004 |
| WO | WO 2004/009036 A2 | 3/2004 |
| WO | WO 2004/018058 A2 | 3/2004 |
| WO | WO 2004/024086 A2 | 3/2004 |
| WO | WO 2004/026226 A1 | 4/2004 |

OTHER PUBLICATIONS

Prodrug [online], [retrieved on Mar. 11, 2007]. Retrieved from the Internet, URL; http://en.wikipedia.org/wiki/Prodrug>.*
RN 154508-94-8, retrieved from CAPLUS on Oct. 3, 2007.*
RN 301154-06-3, retrieved from CAPLUS on Oct. 3, 2007.*
RN 164227-84-3, CAPLUS database, retrieved on Oct. 29, 2008, Katritsky, et al.*
RN 73042-57-6, CAPLUS database, retrieved on Oct. 29, 2008, Pandey, et al.*

* cited by examiner

*Primary Examiner*—Rebecca L Anderson
*Assistant Examiner*—Shawquia Young
(74) *Attorney, Agent, or Firm*—Vinit Kathardekar; Hugo Eng

(57) ABSTRACT

The present invention relates to new indole and benzimidazole compounds and pharmaceutically acceptable salts, esters or prodrugs thereof, compositions of the new compounds together with pharmaceutically acceptable carriers, and uses of the new compounds. The compounds of the invention have the following general formula:

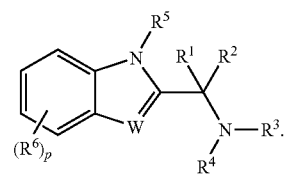

22 Claims, No Drawings

INDOLE AND BENZIMIDAZOLE DERIVATIVES

This application claims the benefit under 35 U.S.C. § 119 (e) of U.S. Provisional Application No. 60/620,385 filed on Oct. 19, 2004, which is hereby incorporated by reference in its entirety.

BACKGROUND OF THE INVENTION

1. Field of the Invention

The present invention relates to substituted indole and benzimidazole compounds as well as pharmaceutically acceptable salts, esters, isomers, mixtures of isomers, derivatives, and prodrugs thereof, compositions of these compounds together with pharmaceutically acceptable carriers, and uses of these compounds.

2. State of the Art

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIF11) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., *Cell* 83:1159-1169, 1995). Mutations in bimC and cut7 genes, which are considered to be homologues of KSP, cause failure in centrosome separation in *Aspergillus nidulans* (Enos, A. P., and N. R. Morris, *Cell* 60:1019-1027, 1990) and *Schizosaccharomyces pombe* (Hagan, I., and M. Yanagida, *Nature* 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of ATRA (Kaiser, A., et al., *J. Biol. Chem.* 274, 18925-18931, 1999). Interestingly, the *Xenopus laevis* Aurora-related protein kinase pEg2 was shown to associate and phosphorylate XlEg5 (Giet, R., et al., *J. Biol. Chem.* 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., *Science* 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., *Biochemistry*, 42:338-349, 2003; Kapoor, T. M., et al., *J. Cell Biol.*, 150:975-988, 2000).

In light of the importance of improved chemotherapeutics, there is a need for KSP inhibitors that are effective in vivo inhibitors of KSP and KSP-related proteins.

SUMMARY OF THE INVENTION

This invention is directed to indole and benzimidazole compounds which modulate the activity of KSP represented by formula I:

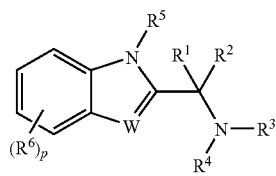

wherein:

W is =CH— or =N—;

$R^1$ is selected from the group consisting of aminoacyl, acylamino, carboxyl, carboxyl ester, aryl, and alkyl optionally substituted with hydroxy or halo;

$R^2$ is selected from the group consisting of hydrogen, optionally substituted alkyl, and aryl;

$R^3$ is —X-A, wherein A is selected from the group consisting of alkyl, aryl, heteroaryl, heterocyclic, and cycloalkyl, all of which may be optionally substituted with 1 to 4 substituents independently selected from the group consisting of alkyl, substituted alkyl, acylamino, heterocyclic, substituted heterocyclic, heterocyclyloxy, substituted heterocyclyloxy, acyl, carboxyl, carboxyl ester, oxo (except as a substituent on substituted aryl or substituted heteroaryl), halo, hydroxy, and nitro;

X is selected from the group consisting of —C(O)—, —C(S)—, —S(O)—, —S(O)$_2$—, and —S(O)$_2$NR—, where R is hydrogen or alkyl and when X is —C(O)—, A is further selected from the group consisting of amino, substituted amino, alkoxy, and substituted alkoxy;

$R^4$ is selected from the group consisting of hydrogen, hydroxy, acyl, alkyl, substituted alkyl, cycloalkyl, substituted cycloalkyl, aryl, substituted aryl, heteroaryl, substituted heteroaryl, heterocyclic, and substituted heterocyclic;

or $R^1$ and $R^4$, together with the carbon atom attached to $R^1$ and the nitrogen atom attached to $R^4$ form a group selected from the group consisting of heterocyclic, substituted heterocyclic, heteroaryl, and substituted heteroaryl;

or when $R^1$ and $R^4$, together with the carbon attached to $R^1$ and nitrogen atom attached to $R^4$ do not form a group selected from the group consisting of heterocyclic, substituted heterocyclic, heteroaryl, and substituted heteroaryl, then $R^3$ and $R^4$, together with the nitrogen atom bound thereto, form a group selected from the group consisting of heterocyclic, substituted heterocyclic, heteroaryl, and substituted heteroaryl;

$R^5$ is -L-A$^1$ where L is selected from the group consisting of —S(O)$_r$— where r is one or two and $C_1$ to $C_2$ straight chain alkylene, optionally substituted with hydroxy, halo and acylamino;

$A^1$ is selected from the group consisting of aryl, substituted aryl, heteroaryl, substituted heteroaryl, heterocyclic, substituted heterocyclic, cycloalkyl and substituted cycloalkyl;

each $R^6$ is independently selected from the group consisting of acyl, acylamino, alkyl, substituted alkyl, alkenyl, substituted alkenyl, alkynyl, substituted alkynyl, alkoxy, substituted alkoxy, amino, substituted amino, aminoacyl, aryl, substituted aryl, aryloxy, substituted aryloxy, carboxyl, carboxyl ester, cyano, cycloalkyl, substituted cycloalkyl, halo, heteroaryl, substituted heteroaryl, heteroaryloxy, substituted heteroaryloxy, heterocyclic, substituted heterocyclic, heterocyclyloxy, substituted heterocyclyloxy, hydroxy, nitro, thiol, alkylthio, substituted alkylthio, arylthio, substituted arylthio, heteroarylthio, and substituted heteroarylthio;

p is equal to 0, 1, 2 or 3;

or pharmaceutically acceptable salts, esters and prodrugs thereof;

with the proviso that when W is =N—, and $A^1$ is substituted phenyl, said substituted phenyl does not include an ortho substituent of the formula $-Q-NR^7R^8$ where Q is a bond, $C_1$ to $C_3$ alkyl, $C_2$ to $C_3$ alkenyl, $C_2$ to $C_3$ alkynyl and $R^7$ and $R^8$ are independently $C_1$ to $C_8$ alkyl or $C_1$ to $C_8$ cycloalkyl optionally substituted with 1 to 3 substituents selected from the group consisting of hydroxy, halo, amino, cyano, nitro, $C_1$ to $C_8$ alkyl, $C_1$ to $C_8$ cycloalkyl, halo $C_1$ to $C_8$ alkyl, $C_1$ to $C_8$ alkoxy, halo $C_1$ to $C_8$ alkoxy, or $R^7$ and $R^8$ jointly with the nitrogen atom to which they are bound form an optionally substituted 3- to 7-membered heterocyclic or an optionally substituted 3- to 7-membered heteroaryl.

DETAILED DESCRIPTION OF THE INVENTION

A. Compounds of the Invention

As stated above, compounds of the invention include those of formula I:

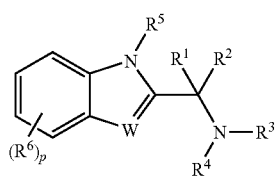

wherein:

W is =CH— or =N—;

$R^1$ is selected from the group consisting of aminoacyl, acylamino, carboxyl, carboxyl ester, aryl, and alkyl optionally substituted with hydroxy or halo;

$R^2$ is selected from the group consisting of hydrogen, optionally substituted alkyl, and aryl;

$R^3$ is —X-A, wherein A is selected from the group consisting of alkyl, aryl, heteroaryl, heterocyclic, and cycloalkyl, all of which may be optionally substituted with 1 to 4 substituents independently selected from the group consisting of alkyl, substituted alkyl, acylamino, heterocyclic, substituted heterocyclic, heterocyclyloxy, substituted heterocyclyloxy, acyl, carboxyl, carboxyl ester, oxo (except as a substituent on substituted aryl or substituted heteroaryl), halo, hydroxy, and nitro;

X is selected from the group consisting of —C(O)—, —C(S)—, —S(O)—, —S(O)$_2$—, and —S(O)$_2$NR—, where R is hydrogen or alkyl and when X is —C(O)—, A is further selected from the group consisting of amino, substituted amino, alkoxy, and substituted alkoxy;

$R^4$ is selected from the group consisting of hydrogen, hydroxy, acyl, alkyl, substituted alkyl, cycloalkyl, substituted cycloalkyl, aryl, substituted aryl, heteroaryl, substituted heteroaryl, heterocyclic, and substituted heterocyclic;

or $R^1$ and $R^4$, together with the carbon atom attached to $R^1$ and the nitrogen atom attached to $R^4$ form a group selected from the group consisting of heterocyclic, substituted heterocyclic, heteroaryl, and substituted heteroaryl;

or when $R^1$ and $R^4$, together with the carbon attached to $R^1$ and nitrogen atom attached to $R^4$ do not form a group selected from the group consisting of heterocyclic, substituted heterocyclic, heteroaryl, and substituted heteroaryl, then $R^3$ and $R^4$, together with the nitrogen atom bound thereto, form a group selected from the group consisting of heterocyclic, substituted heterocyclic, heteroaryl, and substituted heteroaryl;

$R^5$ is -L-$A^1$ where L is selected from the group consisting of —S(O)$_r$— where r is one or two and $C_1$ to $C_2$ straight chain alkylene, optionally substituted with hydroxy, halo and acylamino;

$A^1$ is selected from the group consisting of aryl, substituted aryl, heteroaryl, substituted heteroaryl, heterocyclic, substituted heterocyclic, cycloalkyl and substituted cycloalkyl;

each $R^6$ is independently selected from the group consisting of acyl, acylamino, alkyl, substituted alkyl, alkenyl, substituted alkenyl, alkynyl, substituted alkynyl, alkoxy, substituted alkoxy, amino, substituted amino, aminoacyl, aryl, substituted aryl, aryloxy, substituted aryloxy, carboxyl, carboxyl ester, cyano, cycloalkyl, substituted cycloalkyl, halo, heteroaryl, substituted heteroaryl, heteroaryloxy, substituted heteroaryloxy, heterocyclic, substituted heterocyclic, heterocyclyloxy, substituted heterocyclyloxy, hydroxy, nitro, thiol, alkylthio, substituted alkylthio, arylthio, substituted arylthio, heteroarylthio, and substituted heteroarylthio;

p is equal to 0, 1, 2 or 3;

or pharmaceutically acceptable salts, esters and prodrugs thereof;

with the proviso that when W is =N—, and $A^1$ is substituted phenyl, said substituted phenyl does not include an ortho substituent of the formula $-Q-NR^7R^8$ where Q is a bond, $C_1$ to $C_3$ alkyl, $C_2$ to $C_3$ alkenyl, $C_2$ to $C_3$ alkynyl and $R^7$ and $R^8$ are independently $C_1$ to $C_8$ alkyl or $C_1$ to $C_8$ cycloalkyl optionally substituted with 1 to 3 substituents selected from the group consisting of hydroxy, halo, amino, cyano, nitro, $C_1$ to $C_8$ alkyl, $C_1$ to $C_8$ cycloalkyl, halo $C_1$ to $C_8$ alkyl, $C_1$ to $C_8$ alkoxy, halo $C_1$ to $C_8$ alkoxy, or $R^7$ and $R^8$ jointly with the nitrogen atom to which they are bound form an optionally substituted 3- to 7-membered heterocyclic or an optionally substituted 3- to 7-membered heteroaryl.

In one embodiment, this invention is directed to benzimidazole compounds of formula IA:

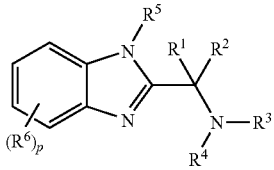

IA wherein $R^1$, $R^2$, $R^3$, $R^4$, $R^5$, $R^6$ and p are as defined above.

In another embodiment, this invention is directed to indole compounds of formula IB:

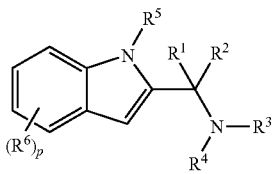

IB wherein $R^1$, $R^2$, $R^3$, $R^4$, $R^5$, $R^6$ and p are as defined above.

In yet another embodiment, the invention is directed to a compound of formula IC:

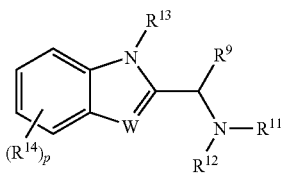

IC wherein
W is =CH— or =N—;
p is equal to 0, 1, 2 or 3;
$R^9$ is alkyl or substituted alkyl;
$R^{11}$ is —$X^1$-$A^2$, wherein $X^1$ is —C(O)— and $A^2$ is selected from the group consisting of alkyl, substituted alkyl, aryl, substituted aryl, heteroaryl, and substituted heteroaryl;
$R^{12}$ is selected from the group consisting of hydrogen, -alkylene-amino, -alkylene-substituted amino, -alkylene-aryl, -alkylene-substituted aryl, -alkylene-heteroaryl, and -alkylene-substituted heteroaryl;
or $R^9$ and $R^{12}$ together with the carbon atom attached to $R^9$ and the nitrogen atom attached to $R^{12}$ form a group selected from the group consisting of heterocyclic, substituted heterocyclic, heteroaryl, and substituted heteroaryl;
or when $R^9$ and $R^{12}$ together with the carbon atom attached to $R^9$ and the nitrogen atom attached to $R^{12}$ do not form a group selected from the group consisting of heterocyclic, substituted heterocyclic, heteroaryl, and substituted heteroaryl, then $R^{11}$ and $R^{12}$, together with the nitrogen atom bound thereto join to form a group selected from the group consisting of heterocyclic, substituted heterocyclic, heteroaryl, and substituted heteroaryl;

$R^{13}$ is -$L^1$-$A^3$, wherein $L^1$ is —S(O)$_r$— where r is 1 or 2 or $C_1$ to $C_2$ straight chain alkylene, and $A^3$ is selected from the group consisting of aryl, substituted aryl, heteroaryl, and substituted heteroaryl;
each $R^{14}$ is independently selected from the group consisting of halo, $C_2$ to $C_3$ alkynyl, $C_2$ to $C_3$ alkenyl, $C_1$ to $C_5$ alkyl, $C_1$ to $C_3$ alkoxy, and phenyl;
or pharmaceutically acceptable salts, esters or prodrugs thereof;
with the proviso that when W is =N—, and $A^1$ is substituted phenyl, said substituted phenyl does not include an ortho substituent of the formula -Q-$NR^7R^8$ where Q is a bond, $C_1$ to $C_3$ alkyl, $C_2$ to $C_3$ alkenyl, $C_2$ to $C_3$ alkynyl and $R^7$ and $R^8$ are independently $C_1$ to $C_8$ alkyl or $C_1$ to $C_8$ cycloalkyl optionally substituted with 1 to 3 substituents selected from the group consisting of hydroxy, halo, amino, cyano, nitro, $C_1$ to $C_8$ alkyl, $C_1$ to $C_8$ cycloalkyl, halo $C_1$ to $C_8$ alkyl, $C_1$ to $C_8$ alkoxy, halo $C_1$ to $C_8$ alkoxy, or $R^7$ and $R^8$ jointly with the nitrogen atom to which they are bound form an optionally substituted 3- to 7-membered heterocyclic or an optionally substituted 3- to 7-membered heteroaryl.

In formulas I, IA, IB and/or IC the following embodiments either alone or in combination with other embodiments include the following:

1. $R^1$ ($R^9$)

In some embodiments of the invention, $R^1$ is alkyl or aryl or $R^1$ is ethyl, isopropyl, t-butyl, or phenyl and is preferably, derived from the corresponding L-amino acid.

2. $R^2$

In some embodiments $R^2$ is hydrogen or methyl. In some embodiments, $R^2$ is alkyl.

3. $R^3$ ($R^{11}$)

In some embodiments, X is —C(O)— and A is aryl or heteroaryl optionally substituted with halo, alkyl, acylamino, nitro, or hydroxy.

In other embodiments, $R^3$ is selected from the group consisting of (2-chloro-6-methylpyridin-4-yl)carbonyl; (5-methylimidazol-4-yl)carbonyl; (dimethylamino)methylcarbonyl; (naphth-2-yl)carbonyl; (pyridin-3-yl)carbonyl; (pyridin-4-yl)carbonyl; 1,5-dimethylpyrazol-3-ylcarbonyl; 1-methyl-5-trifluoromethylpyrazol-4-ylcarbonyl; 1-methyl-5-chloropyrazol-4-ylcarbonyl; 2-(2-aminoethylamido)-4-methylbenzoyl; 2,4-difluorobenzoyl; 2,4-dimethylthiazol-5-ylcarbonyl; 2,6-difluorobenzoyl; 2-aminoethylcarbonyl; 2-aminothiazol-4-ylcarbonyl; 2-chlorobenzoyl; 2-chloropyridin-5-ylcarbonyl; 2-fluorobenzoyl; 2-methoxybenzoyl; 2-methylpyridin-5-ylcarbonyl; 3,4-dichlorobenzoyl; 3,4-dimethylbenzoyl; 3-chlorobenzoyl; 3-fluoro-4-methylbenzoyl; 3-hydroxypyridin-4-ylcarbonyl; 4-aminopyridin-3-ylcarbonyl; 4-bromobenzoyl; 4-chlorobenzoyl; 4-chloropyridin-3-ylcarbonyl; 4-dimethylaminobenzoyl; 4-hydroxybenzoyl; 4-hydroxypyridin-3-ylcarbonyl; 4-methoxybenzoyl; 4-methyl-2-(aminoethylcarbonylamino)benzoyl; 4-methylbenzoyl; 4-methylisoxazol-3-ylcarbonyl; 4-methylpyridin-3-ylcarbonyl; 4-morpholino-N-ylpyridin-3-ylcarbonyl; 4-nitrobenzoyl; 4-t-butylbenzoyl; 4-trifluoromethylbenzoyl; 4-trifluoromethylpyridin-3-ylcarbonyl; 5-chloropyridin-3-ylcarbonyl; 5-methylpyrazol-3-ylcarbonyl; 6-chloropyridin-3-ylcarbonyl; benzoyl; cyclohexylcarbonyl; furan-3-ylcarbonyl; isoxazol-3-ylcarbonyl; phenylsulfonyl; piperidin-4-ylcarbonyl; pyrazin-2-ylcarbonyl; pyridazin-3-ylcarbonyl; pyridazin-4-ylcarbonyl; tetrahydrofuran-2-ylcarbonyl; tetrahydrofuran-3-ylcarbonyl; and thiazol-4-ylcarbonyl.

Additional embodiments of $R^3$ include the following moieties:
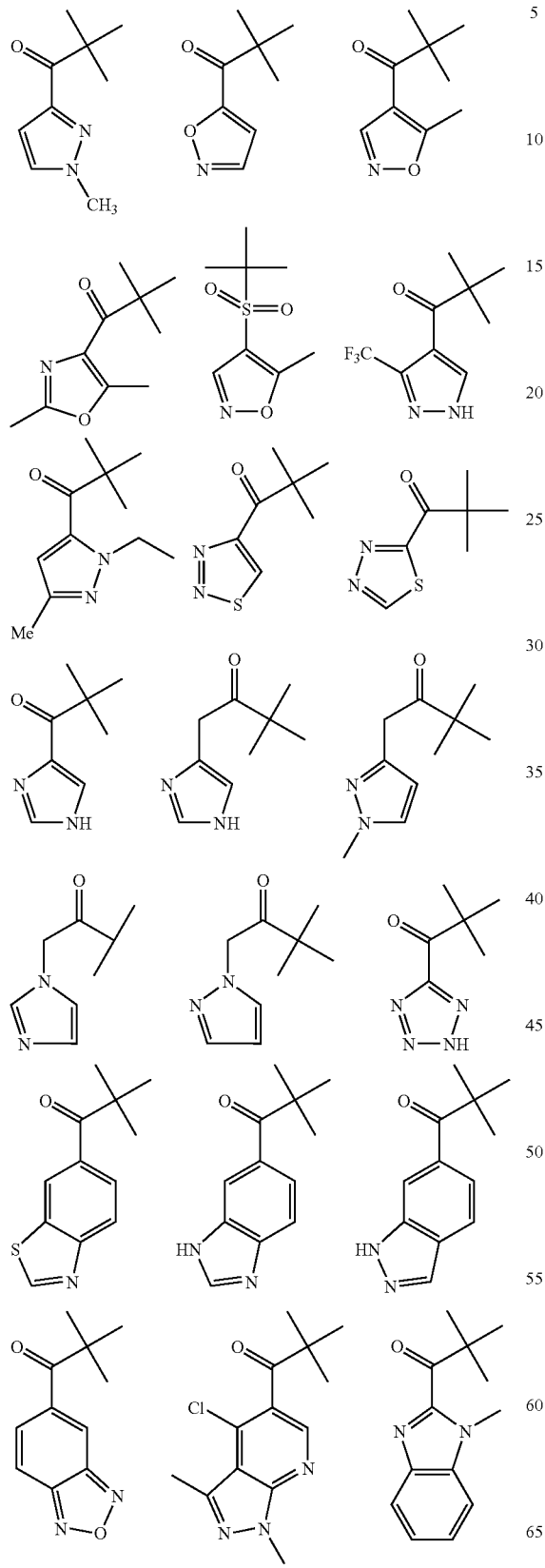
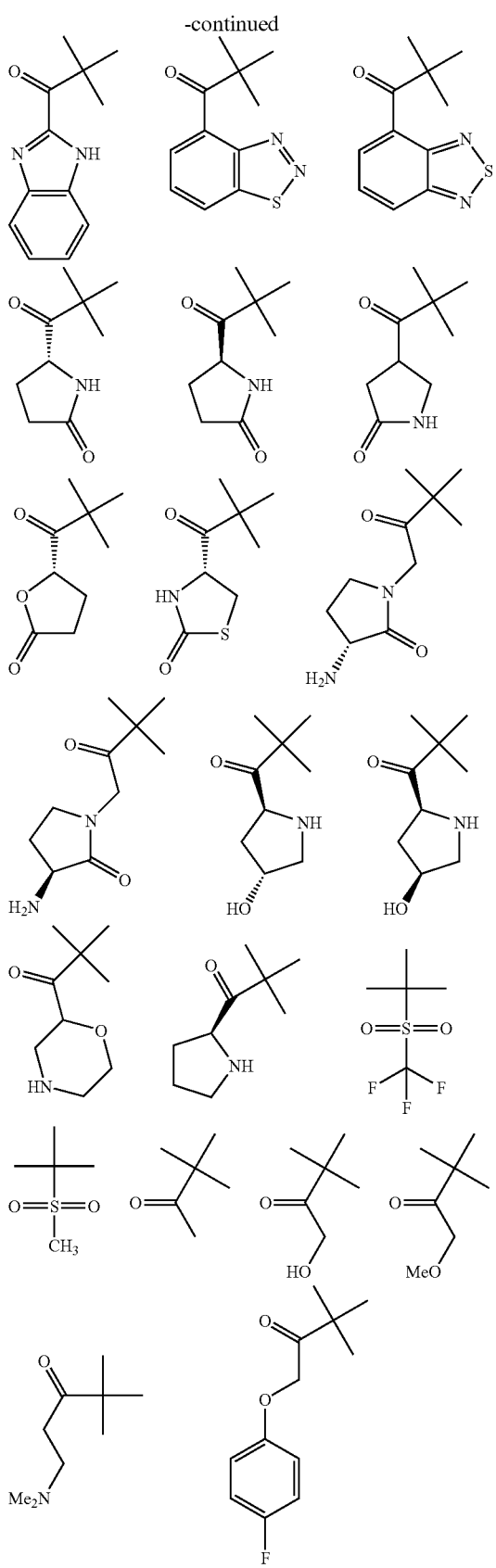
where — indicates the point of attachment.

Particularly preferred embodiments include X-A being selected from the group consisting of 2-aminoethylcarbonyl; 4-methyl-2-(aminoethylcarbonylamino)benzoyl; (naphth-2-yl)carbonyl; (pyridin-3-yl)carbonyl; (pyridin-4-yl)carbonyl; 2-(2-aminoethylamido)-4-methylbenzoyl; 2,4-difluorobenzoyl; 2,6-difluorobenzoyl; 2-fluorobenzoyl; 3,4-dimethylbenzoyl; 3-fluoro-4-methylbenzoyl; 4-bromobenzoyl; 4-chlorobenzoyl; 4-hydroxybenzoyl; 4-methylbenzoyl; 4-nitrobenzoyl; and benzoyl.

4. $R^1$ and $R^4$ ($R^9$ and $R^{12}$)

$R^1$ and $R^4$, together with the carbon atom attached to $R^1$ and the nitrogen atom attached to $R^4$ form a heterocyclic or substituted heterocyclic group and in one embodiment the group is 3-hydroxy-pyrrolidinyl.

5. $R^3$ and $R^4$ ($R^{11}$ and $R^{12}$)

In embodiments when $R^1$ and $R^4$ are not cyclized as described above, then $R^3$ and $R^4$ together with the nitrogen atom attached thereto can join to form a substituted heterocyclic group. In one embodiment the group is 2-aminoethyl-5-methyl-8-oxo-7H-quinazolin-1-yl.

6. $R^4$ ($R^{11}$)

In one embodiment, $R^4$ is selected from the group consisting of hydrogen, alkyl and substituted alkyl.

In other embodiments, $R^4$ is selected from the group consisting of hydrogen; (aminomethylcarbonyl)aminoethyl; 2,2-dimethyl-3-(4-methylpiperazin-1-yl)propyl; 2,2-dimethyl-3-dimethylaminopropyl; 2-aminoethyl; 2-hydroxyethyl-3-aminopropyl; 2-hydroxypyridin-4-ylmethyl; 2-hydroxypyridin-5-ylmethyl; 3-(1-cyanourea)propyl; 3-(benzylamino)propyl; 3-(cyclobutylamino)propyl; 3-(cyclohexylmethylamino)propyl; 3-(diethylamino)propyl; 3-(isopropylamino)propyl; 3-(phenylcarbonyloxy)propyl; 3-[(3-trifluoromethylpyridin-6-yl)amino]propyl; 3-[(5-pyridin-3-yloxyindazol-3-yl)methylamino]propyl; 3-[(6-fluoroindazol-3-yl)methylamino]propyl; 3-[(aminomethyl-carbonyl)amino]propyl; 3-[5-cyanopyridin-2-yl]propyl; 3-[[5-(pyridin-3-yloxy)indazol-3-yl]methylamino]propyl; 3-amino-3-(aminocarbonyl-methyl)propyl; 3-aminopropyl; 3hydroxypropyl; 3-methylsulfonylaminopropyl; 3-ureapropyl; 4-methylbenzyl; 5-methoxyindazol-3-ylmethyl; benzyl; piperidin-3-ylmethyl; piperidin-4-yl; pyrrolidin-2-ylmethyl;

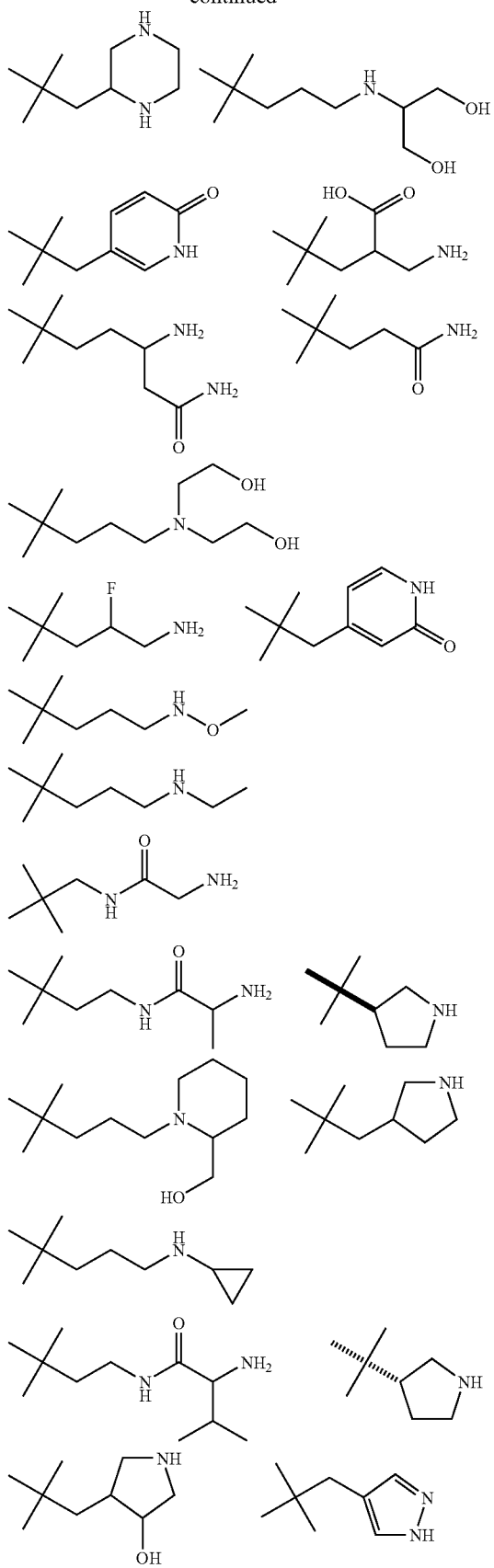

-continued

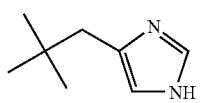
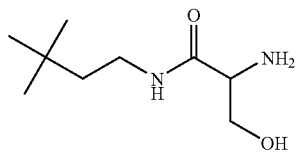
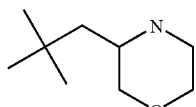
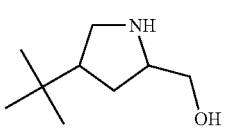
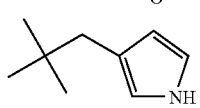

where — indicates the point of attachment.

More preferably, $R^4$ is selected from the group consisting of hydrogen; 3-(1-cyanourea)propyl; 3-(benzylamino)propyl; 3-(cyclobutylamino)propyl; 3-(cyclohexylmethylamino)propyl; 3-(diethylamino)propyl; 3-(isopropylamino)propyl; 3-aminopropyl; 3-ureapropyl; 4-methylbenzyl; and imidazol-4-ylmethyl.

7. $R^5$ ($R^{13}$)

In one embodiment of the invention L is —$SO_2$— or —$CH_2$— and $A^1$ is optionally substituted aryl. In other embodiments, $R^5$ is selected from the group consisting of 2,4-difluorobenzyl; 2-methylbenzyl; 3-(methylamido)benzyl; 3,5-difluorobenzyl; 3-chlorobenzyl; 3-fluorobenzyl; 3-hydroxybenzyl; 3-methylbenzyl; 4-chlorobenzyl; 4-methylbenzyl; benzyl; and thiazol-4-ylmethyl.

Particularly preferred $R^5$ groups are selected from the group consisting of: 3-(methylamido)benzyl; 3,5-difluorobenzyl; 3-chlorobenzyl; 3-fluorobenzyl; 3-hydroxybenzyl; 4-chlorobenzyl; and benzyl.

8. $R^6$

When p is not zero, then $R^6$ is selected from the group consisting of propargyl; bromo; —$CF_3$; chloro; ethyl; ethynyl; fluoro; methoxy; methyl; phenyl; and vinyl.

In some embodiments, $R^6$ is selected from the following bromo; chloro; ethyl; methoxy; methyl; propargyl; vinyl; fluoro; and phenyl.

9. $R^{14}$

In some embodiments, $R^{14}$ is propargyl, bromo, —$CF_3$, chloro, ethyl, ethynyl, fluoro, methoxy, methyl, phenyl, or vinyl. In some embodiments, $R^{14}$ is bromo, chloro, ethyl, methoxy, methyl, propargyl, vinyl, fluoro, or phenyl.

10. p

In some embodiments, p is zero or one.

Indole and benzimidazole compounds within the scope of this invention are exemplified by those set forth in Tables 1 and 2 as follows.

TABLE 1

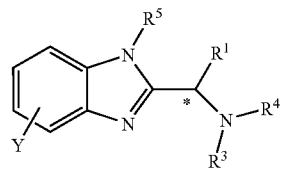

| Cmpd No. | $R^1$ | $R^3$ | $R^4$ | $R^5$ | $R^6$ |
|---|---|---|---|---|---|
| 1 | isopropyl | 4-chlorobenzoyl | 3-aminopropyl | benzyl | H |
| 2 | isopropyl | 4-methylbenzoyl | 3-aminopropyl | benzyl | H |
| 3 | isopropyl | 4-methylbenzoyl | 3-aminopropyl | benzyl | 5-methyl |
| 4 | isopropyl | 4-methylbenzoyl | 3-aminopropyl | benzyl | 5-chloro |
| 5 | isopropyl | 4-methylbenzoyl | 3-aminopropyl | 4-chlorobenzyl | 6-fluoro |
| 6 | ethyl | 4-methylbenzoyl | 3-aminopropyl | benzyl | 5-chloro |
| 7 | isopropyl | 4-bromobenzoyl | 3-aminopropyl | benzyl | H |
| 8 | isopropyl | 4-methylbenzoyl | 3-aminopropyl | benzyl | 5-bromo |
| 9 | ethyl | benzoyl | 3-aminopropyl | benzyl | 5-bromo |
| 10 | ethyl | 4-methylbenzoyl | 3-aminopropyl | benzyl | 5-bromo |
| 11 | isopropyl | 4-methylbenzoyl | 3-aminopropyl | 3-hydroxybenzyl | 5-methyl |
| 12 | isopropyl | 4-methylbenzoyl | 3-aminopropyl | 3-fluorobenzyl | 5-methyl |
| 13 | isopropyl | 4-methylbenzoyl | 3-aminopropyl | benzyl | 5-ethyl |
| 14 | isopropyl | 4-methylbenzoyl | 3-aminopropyl | 3-hydroxybenzyl | 5-ethyl |
| 15 | isopropyl | 4-methylbenzoyl | 3-ammopropyl | 3-fluorobenzyl | 5-ethyl |
| 16 | isopropyl | 2-aminoethylcarbonyl | 4-methylbenzyl | benzyl | 5-bromo |
| 17 | isopropyl | 4-methylbenzoyl | 3-aminopropyl | benzyl | 5-vinyl |
| 18 | isopropyl | 4-methylbenzoyl | 3-aminopropyl | benzyl | 5-methoxy |
| 19 | isopropyl | 4-methylbenzoyl | 3-aminopropyl | benzyl | phenyl |
| 20 | isopropyl | 4-methyl-2-(aminoethylcarbonylamino)-benzoyl | H | benzyl | 5-bromo |
| 21 | $R^1/R^4$ = 4-hydroxypyrrolidin-2-yl | 4-methylbenzoyl | — | 3-hydroxybenzyl | 5-methyl |
| 22 | isopropyl | 4-methylbenzoyl | 3-aminopropyl | benzyl | 5-propargyl |
| 23 | isopropyl | $R^3/R^4$ = 2-aminoethyl-5-methyl-8-oxo-7H-quinazolin-1-yl | — | benzyl | 5-bromo |
| 24 | isopropyl | 3-fluoro-4-methylbenzoyl | 3-aminopropyl | 3-fluorobenzyl | 5-methyl |
| 25 | isopropyl | benzoyl | 3-aminopropyl | 3-fluorobenzyl | 5-methyl |

TABLE 1-continued

![structure with R5 on N, R1, R3, R4, N, Y benzimidazole]

| Cmpd No. | R¹ | R³ | R⁴ | R⁵ | R⁶ |
|---|---|---|---|---|---|
| 26 | isopropyl | 2,4-difluorobenzoyl | 3-aminopropyl | 3-fluorobenzyl | 5-methyl |
| 27 | isopropyl | 3,4-dimethylbenzoyl | 3-aminopropyl | 3-fluorobenzyl | 5-methyl |
| 28 | isopropyl | 4-methylbenzoyl | 3-aminopropyl | 3-(methylamido)benzyl | 5-bromo |
| 29 | isopropyl | 2,6-difluorobenzoyl | 3-aminopropyl | 3-fluorobenzyl | 5-methyl |
| 30 | isopropyl | 2-fluorobenzoyl | 3-aminopropyl | 3-fluorobenzyl | 5-methyl |
| 31 | isopropyl | benzoyl | 3-aminopropyl | 3-chlorobenzyl | 5-bromo |
| 32 | isopropyl | 4-nitrobenzoyl | 3-aminopropyl | 3-fluorobenzyl | 5-methyl |
| 33 | isopropyl | (pyridin-3-yl)carbonyl | 3-aminopropyl | 3-fluorobenzyl | 5-methyl |
| 34 | isopropyl | (pyridin-4-yl)carbonyl | 3-aminopropyl | 3-fluorobenzyl | 5-methyl |
| 35 | isopropyl | (naphth-2-yl)carbonyl | 3-aminopropyl | 3-fluorobenzyl | 5-methyl |
| 36 | t-butyl | benzoyl | 3-aminopropyl | 3-fluorobenzyl | 5-methyl |
| 37 | isopropyl | 4-hydroxybenzoyl | 3-aminopropyl | 3-fluorobenzyl | 5-methyl |
| 38 | isopropyl | 4-methylbenzoyl | 3-(benzylamino)propyl | benzyl | 5-chloro |
| 39 | isopropyl | 4-methylbenzoyl | 3-(cyclohexylmethylamino)propyl | benzyl | 5-chloro |
| 40 | t-butyl | benzoyl | 3-aminopropyl | benzyl | H |
| 41 | isopropyl | 4-methylbenzoyl | 3-(isopropylamino)propyl | benzyl | 5-chloro |
| 42 | isopropyl | 4-methylbenzoyl | 3-(diethylamino)propyl | benzyl | 5-chloro |
| 43 | isopropyl | 4-methylbenzoyl | 3-(cyclobutylamino)propyl | benzyl | 5-chloro |
| 44 | isopropyl | benzoyl | 3-aminopropyl | 3,5-difluorobenzyl | 5-bromo |
| 48 | isopropyl | 4-methylbenzoyl | 3-(N-cyanourea)propyl | benzyl | 5-chloro |
| 49 | isopropyl | 4-methylbenzoyl | 3-ureapropyl | benzyl | 5-chloro |
| 50 | isopropyl | benzoyl | imidazol-4-ylmethyl | 3-fluorobenzyl | 5-methyl |

The symbol (*) indicates a chiral center. Unless otherwise indicated, this chiral center contemplates both the (R) and the (S) configuration as well as mixtures thereof. Other chiral centers may also be present in the compound and unless otherwise indicated, the (R) and the (S) configuration are contemplated.

TABLE 2

![indole structure with R5, R1, R3, R4, Y]

| Cmpd No. | Y | R¹ | R³ | R⁴ | R⁵ |
|---|---|---|---|---|---|
| 45 | 5-chloro | isopropyl | benzoyl | 3-aminopropyl | benzyl |
| 46 | 5-chloro | isopropyl | 4-methylbenzoyl | 3-aminopropyl | benzyl |
| 47 | 5-chloro | isopropyl | benzoyl | 3-aminopropyl | phenylsulfonyl |

The symbol (*) indicates a chiral center. Unless otherwise indicated, this chiral center contemplates both the (R) and the (S) configuration as well as mixtures thereof. Other chiral centers may also be present in the compound and unless otherwise indicated, the (R) and the (S) configuration are contemplated.

Representative Compounds of the Invention

Specific compounds within the scope of this invention are exemplified in Table 3 in the experimental section.

ALTERNATIVE EMBODIMENTS

In an alternative embodiment, the invention relates to compounds of the invention include those of formula II:

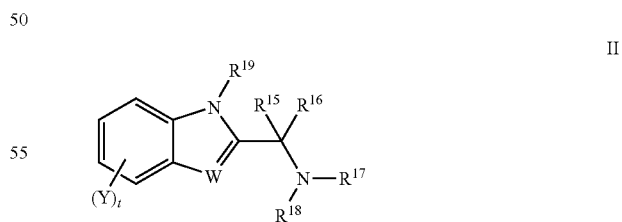

II wherein:
$R^{15}$ is selected from the group consisting of aminoacyl, acylamino, carboxyl, carboxyl ester, aryl, $C_1$ to $C_8$ alkyl optionally substituted with hydroxy or halo;
$R^{16}$ is selected from the group consisting of hydrogen, $C_1$ to $C_8$ alkyl, and aryl;
$R^{17}$ is —$X^2$-$A^3$, wherein $A^3$ is selected from the group consisting of alkyl, aryl, heteroaryl, heterocyclic, and cycloalkyl, all of which may be optionally substituted with 1 to 4 substituents independently selected from the group consisting of $C_1$ to $C_8$ alkyl, $C_1$ to $C_8$ substituted alkyl, $C_1$ to $C_8$ alkoxy, $C_1$ to $C_8$ substituted alkoxy, amino, substituted amino, heterocyclic, substituted heterocyclic, heterocyclyloxy, substituted heterocyclyloxy, acyl, carboxyl, carboxyl ester, oxo (not included as a substituent on substituted aryl or substituted heteroaryl), halo, hydroxy, and nitro, and $X^2$ is selected from the group consisting of —C(O)—, —C(S)—, —S(O)—, —S(O)$_2$—, and —S(O)$_2$NR—, where R is hydrogen or $C_1$ to $C_8$ alkyl and when $X^2$ is —C(O)—, $A^3$ is further selected from the group consisting of amino, substituted amino, alkoxy, and substituted alkoxy;

$R^{18}$ is selected from the group consisting of hydrogen, alkylene-aminoacyl, alkylene-oxyacyl, alkylene-OH, [alkylene]$_q$-nitrogen-containing heterocyclic, -[alkylene]$_q$-substituted nitrogen-containing heterocyclic, -[alkylene]$_q$-nitrogen containing heteroaryl, -[alkylene]$_q$- substituted nitrogen-containing heteroaryl, -[alkylene]$_q$-NR$^{19}$R$^{20}$, -[alkylene]$_q$-aryl, and -[alkylene]$_q$-substituted aryl, wherein q is zero or one, alkylene is a $C_1$ to $C_8$ straight chain alkylene group optionally mono or disubstituted with one or two substituents independently selected from the group consisting of amino, substituted amino, hydroxy, alkyl, substituted alkyl, carboxyl, carboxyl ester, oxo, and halo, $R^{19}$ and $R^{20}$ are independently selected from the group consisting of hydrogen, $C_1$ to $C_8$ alkyl, $C_1$ to $C_8$ substituted alkyl, cyano, aminoacyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl and substituted cycloalkyl or when $R^{19}$ is hydrogen, $R^{20}$ is further selected from the group consisting of hydroxy, alkoxy, or substituted alkoxy;

or $R^{15}$ and $R^{18}$, together with the carbon atom attached to $R^{15}$ and the nitrogen atom attached to $R^{18}$ form a heterocyclic, unsaturated heterocyclic, substituted heterocyclic or substituted unsaturated heterocyclic group;

$R^{19}$ is -L$^2$-A$^4$ where L$^2$ is selected from the group consisting of —S(O)$_r$— where r is one or two and $C_1$ to $C_2$ straight chain alkylene, optionally substituted with hydroxy, halo or acylamino and A$^4$ is selected from the group consisting of aryl, substituted aryl, heteroaryl, substituted heteroaryl, heterocyclic, substituted heterocyclic, cycloalkyl and substituted cycloalkyl;

W is =CH— or =N—;

Y is selected from the group consisting of acyl, acylamino, alkyl, substituted alkyl, alkenyl, substituted alkenyl, alkynyl, substituted alkynyl, alkoxy, substituted alkoxy, amino, substituted amino, aminoacyl, aryl, substituted aryl, aryloxy, substituted aryloxy, carboxyl, carboxyl ester, cyano, cycloalkyl, substituted cycloalkyl, halo, heteroaryl, substituted heteroaryl, heteroaryloxy, substituted heteroaryloxy, heterocyclic, substituted heterocyclic, heterocyclyloxy, substituted heterocyclyloxy, hydroxy, nitro, thiol, alkylthio, substituted alkylthio, arylthio, substituted arylthio, heteroarylthio, and substituted heteroarylthio;

t is equal to 0, 1, 2 or 3;

provided that when W is =N—, and A$^4$ is substituted phenyl, said substituted phenyl does not include an ortho substituent of the formula Q-NR$^{22}$R$^{23}$ where Q is a bond, $C_1$ to $C_3$ alkyl, $C_2$ to $C_3$ alkenyl, $C_2$ to $C_3$ alkynyl and R$^{22}$ and R$^{23}$ are independently $C_1$ to $C_8$ alkyl or $C_1$ to $C_8$ cycloalkyl optionally substituted with 1 to 3 substituents selected from the group consisting of hydroxy, halo, amino, cyano, nitro, $C_1$ to $C_8$ alkyl, $C_1$ to $C_8$ cycloalkyl, halo-$C_1$ to $C_8$ alkyl, $C_1$ to $C_8$ alkoxy, halo-$C_1$ to $C_8$ alkoxy, or R$^{22}$ and R$^{23}$ jointly with the nitrogen atom to which they are bound form a 3 to 7 membered heterocyclic group;

or pharmaceutically acceptable salts, esters and prodrugs thereof.

Methods and Compositions of the Invention

Also provided is a composition comprising a compound of formula I, IA, IB and IC (including mixtures and/or salts thereof) and a pharmaceutically acceptable excipient or carrier.

In another aspect, the present invention provides methods of treating a mammalian patient suffering from a disorder mediated, at least in part, by KSP. Thus, the present invention provides methods of treating a mammalian patient in need of such treatment comprising administering to the patient a therapeutically effective amount of a compound of formula I, IA, IB, IC and/or II (including mixtures thereof) either alone or in combination with other anticancer agents.

B. Definitions and Overview

As discussed above, the present invention is directed to new substituted imidazole compounds.

It is to be understood that the terminology used herein is for the purpose of describing particular embodiments only and is not intended to limit the scope of the present invention. It must be noted that as used herein and in the claims, the singular forms "a," and "the" include plural referents unless the context clearly dictates otherwise. In this specification and in the claims which follow, reference will be made to a number of terms which shall be defined to have the following meanings:

As used herein, "alkyl" refers to monovalent saturated aliphatic hydrocarbyl groups having from 1 to 8 carbon atoms, preferably 1 to 6, and more preferably 1 to 3 carbon atoms. The alkyl group may be straight chain or branched. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, spirocycloalkyl, heteroaryl, substituted heteroaryl, heterocyclic, substituted heterocyclic, —SO$_2$-alkyl, and —SO$_2$-substituted alkyl.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) or (—CH(CH$_3$)CH$_2$—) and the like.

"Alkoxy" refers to the group "alkyl-O-" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NR$^{30}$R$^{30}$ where each R$^{30}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{30}$ is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxyacyl" or "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation. Examples of alkynyl include, but are not limited to, propargyl, butyne, pentyne, etc.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic with the proviso that any hydroxy substitution is not attached to an acetylenic carbon atom.

"Amino" refers to the group —NH$_2$.

"Cyano" refers to the group —CN.

"Substituted amino" refers to the group —NR$^{31}$R$^{32}$ where R$^{31}$ and R$^{32}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, cyano, aminoacyl, —SO$_2$-alkyl, —SO$_2$-substituted alkyl, and where R$^{31}$ and R$^{32}$ are joined, together with the nitrogen bound thereto to form a heterocyclic or substituted heterocyclic group provided that R$^{31}$ and R$^{32}$ are both not hydrogen. When R$^{31}$ is hydrogen and R$^{32}$ is alkyl, the substituted amino group is sometimes referred to herein as alkylamino. When R$^{31}$ and R$^{32}$ are alkyl, the substituted amino group is sometimes referred to herein as dialkylamino. When referring to a monosubstituted amino, it is meant that either R$^{31}$ or R$^{32}$ is hydrogen but not both. When referring to a disubstituted amino, it is meant that neither R$^{31}$ or R$^{32}$ is hydrogen.

"Acylamino" refers to the groups —NR$^{33}$C(O)alkyl, —NR$^{33}$C(O)substituted alkyl, —NR$^{33}$C(O)cycloalkyl, —NR$^{33}$C(O)substituted cycloalkyl, —NR$^{33}$C(O)alkenyl, —NR$^{33}$C(O)substituted alkenyl, —NR$^{33}$C(O)alkynyl, —NR$^{33}$C(O)substituted alkynyl, —NR$^{33}$C(O)aryl, —NR$^{33}$C(O)substituted aryl, —NR$^{33}$C(O)heteroaryl, —NR$^{33}$C(O)substituted heteroaryl, —NR$^{33}$C(O)heterocyclic, and —NR$^{33}$C(O)substituted heterocyclic where R$^{33}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) in which the condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl ester, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to —COOR$^{33}$, where R$^{33}$ is defined above.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Spirocycloalkyl" refers to cyclic groups from 3 to 10 carbon atoms having a cycloalkyl ring with a spiro union (the union formed by a single atom which is the only common member of the rings) as exemplified by the following structure:

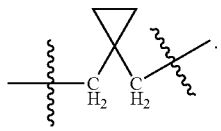

"Substituted cycloalkyl" refers to a cycloalkyl group, having from 1 to 5 substituents selected from the group consisting of alkyl, substituted alkyl, oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, substituted heterocyclic, —SO$_2$-alkyl and —SO$_2$-cycloalkyl "Halo" or "halogen" refers to fluoro, chloro, bromo and iodo and preferably is fluoro or chloro.

The term "haloalkyl" refers to a branched, straight-chain or cyclic alkyl group, substituted with 1 or more halogen atoms (e.g., "halo C$_1$ to C$_8$ alkyl" groups have from 1 to 8 carbon atoms). The term "haloalkoxy" refers to a haloalkyl group as defined above attached via an oxygen bridge. "Halo C$_1$ to C$_8$ alkoxy" groups have 1 to 8 carbon atoms.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

The term "nitrogen-containing heteroaryl" refers to a heteroaryl group wherein at least one of the ring members is a nitrogen. The term "substituted nitrogen-containing heteroaryl" refers to a substituted heteroaryl group wherein at least one ring member is a nitrogen.

"Heteroaryloxy" refers to the group —O-heteroaryl and "substituted heteroaryloxy" refers to the group —O-substituted heteroaryl wherein heteroaryl and substituted heteroaryl are as defined herein.

"Heterocycle" or "heterocyclic" or "heterocycloalkyl" or "heterocyclyl" refers to a saturated or unsaturated (but not aromatic) group having a single ring or multiple condensed rings, including fused, pendant, and spiro ring systems, from 1 to 10 carbon atoms and from 1 to 4 hetero atoms selected from the group consisting of nitrogen, sulfur or oxygen within the ring wherein, in fused ring systems, one ring is a heterocyclic ring and one or more the rings can be cycloalkyl, aryl or heteroaryl. In one embodiment, the nitrogen and/or sulfur atom(s) of the heterocyclic group are optionally oxidized to provide for the N-oxide, sulfinyl, and sulfonyl moieties.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

The term "nitrogen-containing heterocyclic" refers to a heterocyclic group wherein at least one of the ring members is a nitrogen atom. The term "substituted nitrogen-containing heterocyclic" refers to a substituted heterocyclic group wherein at least one of the ring members is a nitrogen atom.

"Thiol" refers to the group —SH.

"Alkylthio" or "thioalkoxy" refers to the group —S-alkyl.

"Substituted alkylthio" or "substituted thioalkoxy" refers to the group —S-substituted alkyl.

"Arylthio" refers to the group —S-aryl, where aryl is defined above.

"Substituted arylthio" refers to the group —S-substituted aryl, where substituted aryl is defined above.

"Heteroarylthio" refers to the group —S-heteroaryl, where heteroaryl is defined above.

"Substituted heteroarylthio" refers to the group —S-substituted heteroaryl, where substituted heteroaryl is defined above.

"Heterocyclicthio" refers to the group —S-heterocyclic and "substituted heterocyclicthio" refers to the group —S-substituted heterocyclic, where heterocyclic and substituted heterocyclic are defined above.

"Heterocyclyloxy" refers to the group heterocyclyl-O— and "substituted heterocyclyloxy refers to the group substituted heterocyclyl-O— where heterocyclyl and substituted heterocyclyl are defined above.

"Cycloalkylthio" refers to the group —S-cycloalkyl and "substituted cycloalkylthio" refers to the group —S-substituted cycloalkyl, where cycloalkyl and substituted cycloalkyl are defined above.

"Biological activity" as used herein refers to an inhibition concentration when tested in at least one of the assays outlined in Example 7 or 8 or a decrease in optical density as tested in Example 9.

As used herein, the term "pharmaceutically acceptable salts" refers to the nontoxic acid or alkaline earth metal salts of the compounds of formula I, IA, IB, IC and II. These salts can be prepared in situ during the final isolation and purification of the compounds of formula I, IA, IB, IC and II, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quarternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula I, IA, IB, IC and II, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which hydrolyze in vivo and include those that break down in the human body to leave the parent compound, a salt thereof, or a pharmaceutically active metabolite. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound or a pharmaceutically active metabolite of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxy group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

C. Compound Preparation

The compounds of this invention can be prepared from readily available starting materials using the following general methods and procedures. Unless otherwise indicated, the starting materials are commercially available and well known in the art. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Third Edition, Wiley, New York, 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Compounds in the present invention may be better understood by the following synthetic schemes that illustrate methods for the synthesis of compounds of the invention. Unless otherwise indicated, the reagents used in the following examples are commercially available and may be purchased from vendors such as Sigma-Aldrich Company, Inc. (Milwaukee, Wis., USA) or are known in the art. Benzimidazole compounds may be synthesized by Scheme 1 below:

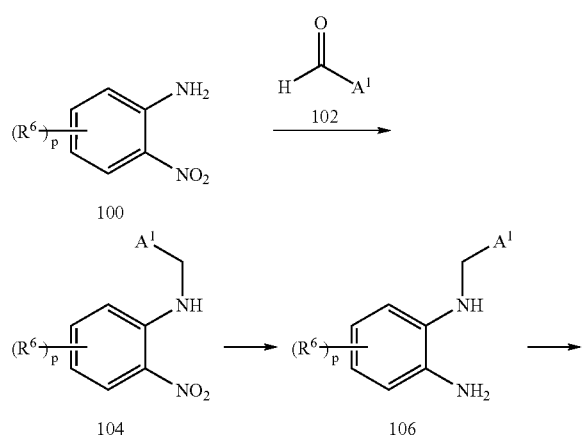

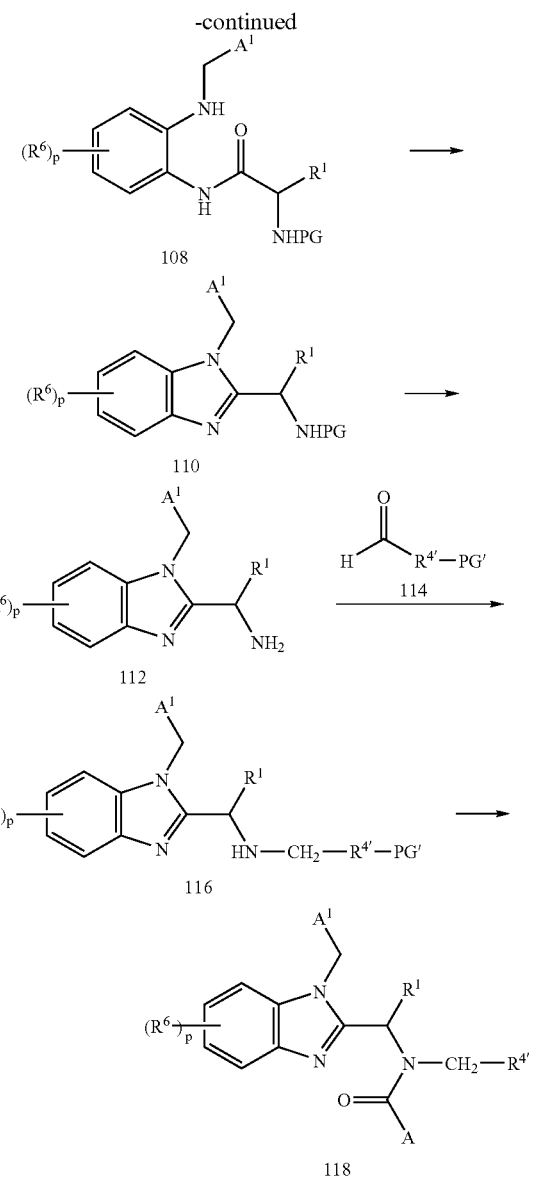

A, $A^1$, $R^1$, $R^3$, $R^6$ and p are as defined herein
PG is a suitable nitrogen-protecting group, such as Boc
PG' is another suitable nitrogen-protecting group, such as phthalimide
$CH_2$—$R^{4'}$ is $R^4$, where $R^4$ is as defined herein Specifically, in Scheme 1, an appropriately substituted nitroaryl amine 100 is combined with aldehyde 102 in a suitable solvent, such as dichloromethane under reductive amination conditions in the presence of a suitable reducing agent such as sodium borohydride. The reaction is stirred at room temperature until complete. The resulting substituted amine 104 can be recovered and optionally purified by conventional methods, such as precipitation, filtration, evaporation, crystallization, chromatography, and the like. Alternatively, the substituted amine 104 can be used in the next step without purification or isolation.

Compounds of the invention when $R^5$ is L-$A^1$ and L is —$S(O)_r$—, may be synthesized using a suitable sulfonyl chloride. Descriptions of various sulfonyl chlorides may be found, for example, in U.S. Pat. No. 6,489,300, which is hereby incorporated by reference.

The nitro group on the substituted amine 104 is then reduced using a reducing agent, such as zinc or iron, under acidic conditions to provide the diamine 106. The resulting diamine 106 is then recovered and optionally purified by conventional methods, such as precipitation, filtration, evaporation, crystallization, chromatography, and the like. Alternatively, the diamine 106 can be used in the next step without further purification or isolation.

The diamine is then coupled with a stoichiometric equivalent or a slight excess of an appropriately amino protected (PG) α-amino acid 107 (not shown). The amino acid is preferably a known amino acid or can be prepared from known compounds by conventional synthetic procedures. Further, the amino acid selected may be in either (D) or (L) configuration or a racemic mixture to produce the appropriate (R) or (S) configuration or racemic mixture of compound 108. Coupling proceeds via conventional amidation conditions well known in the art typically in the presence of a suitable coupling agent, such as TBTU (N,N,N',N'-tetramethyl-O-(benzotraizol-1-yl)uronium tetrafluoroborate). It should be noted that amino acid 107 is typically commercially available as are α,α-disubstituted amino acids (PG-NH—C($R^1$)($R^2$)—COOH). Upon substantial completion of the reaction, typically 8 to 12 h, the resulting substituted diamine 108 can be recovered and optionally purified by conventional methods, such as precipitation, filtration, evaporation, crystallization, chromatography, and the like. Alternatively, the substituted diamine 108 can be used in the next step without purification or isolation.

Substituted diamine 108 is then treated under cyclization conditions which include, for example, heating a solution of the diamine for 2 to 4 h at a temperature of from about 100 to about 110° C., under acidic conditions to provide the substituted arylimidazole 110. The reaction is continued until substantially complete to afford the substituted arylimidazole 110. This product can be recovered and optionally purified by conventional methods, such as precipitation, filtration, evaporation, crystallization, chromatography, and the like. Alternatively, the substituted arylimidazole 110 can be used in the next step without purification.

The protecting group of substituted arylimidazole 110 is removed by conventional techniques to provide amine 112. The amine 112 can then be recovered and optionally purified by conventional methods, such as precipitation, filtration, evaporation, crystallization, chromatography, and the like.

Amine 112 is reacted under conventional reductive amination conditions as described above with aldehyde 114 to provide for substituted amine 116 which is then recovered and optionally purified by conventional methods such as precipitation, filtration, evaporation, chromatography and the like. Alternatively, substituted amine 116 can be used directly in the next step without purification and/or isolation.

Substituted amine 116 is then reacted under conventional amidation conditions with an appropriate acyl chloride. Any protecting groups, such as PG', remaining on the resulting amide product, 118 can be removed by conventional procedures and the product can be recovered and purified by conventional methods, such as precipitation, filtration, evaporation, crystallization, chromatography and the like.

Examples of commercially available 1-amino-2-nitroaryl and 1-amino-2-nitro heteroaryl compounds include, for example, 2-nitroaniline, 2-fluoro-5-nitroaniline, 4-fluoro-2-nitroaniline, 2-chloro-5-nitroaniline, 4-chloro-2-nitroaniline, 2-bromo-5-nitroaniline, 4-methyl-2-nitroaniline, 4-amino-3-nitrobenzonitrile, 2-amino-3-nitropyridine, and the like. Derivation of such compounds into other starting materials useful in Scheme 1 above is well within the skill of the art.

It will be well within the skill of the art to modify the above preparation to synthesize other imidazole compounds of the invention.

Indole compounds of this invention may be synthesized following scheme 2 below:

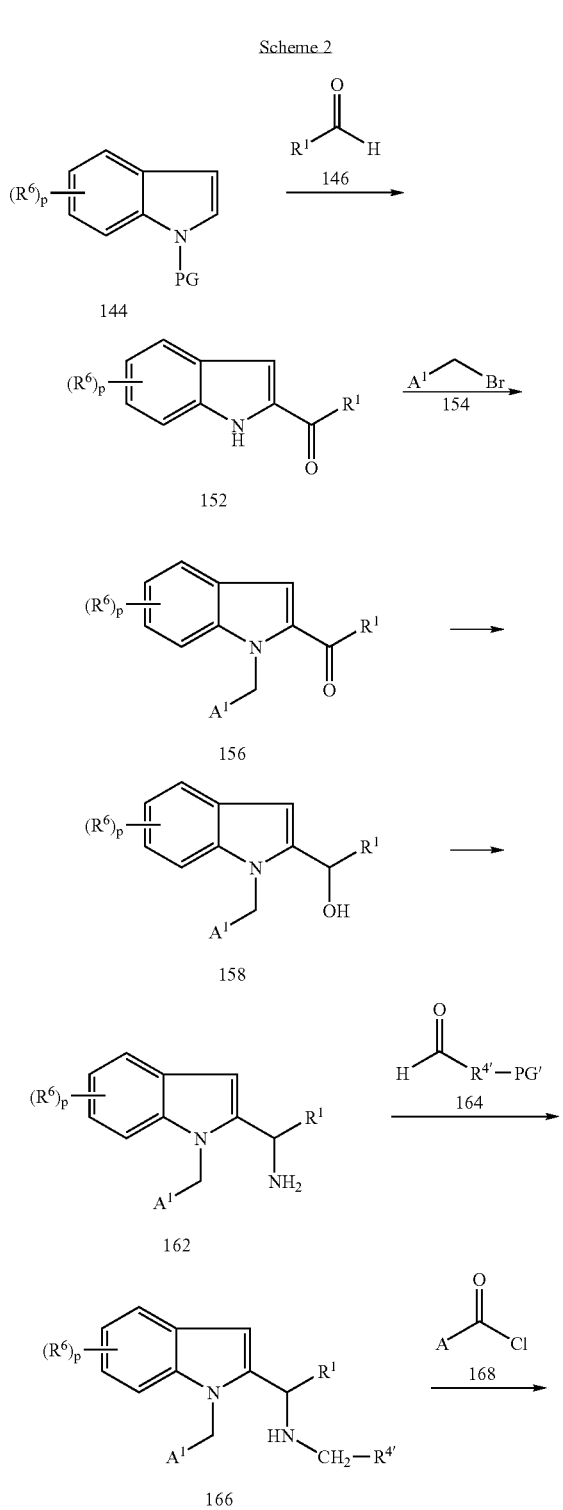

-continued

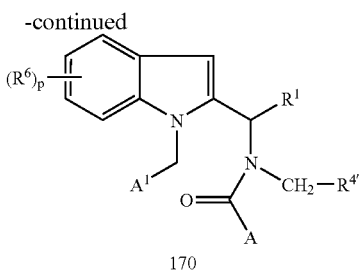

170

A, A¹, R¹, R³, R⁶ and p are as defined herein
PG is a suitable nitrogen-protecting group, such as Boc
PG' is another suitable nitrogen-protecting group, such as phthalimide
CH₂—R⁴' is R⁴, where R⁴ is as defined herein Specifically in Scheme 2, an appropriately protected indole 144 is combined with a slight excess of a suitable alkyl lithium, such as n-butyl lithium, in a suitable solvent such as tetrahydrofuran (THF). The protected indole 144 can be synthesized by protecting a commercially available indole with a protecting group under conventional means. Then, the mixture is warmed to effect anion formation (not shown) and subsequently cooled. A solution of aldehyde 146 is added slowly. The resulting alcohol is then oxidized to the corresponding ketone using conventional means. Then, the protecting group is removed from the nitrogen using conventional means. The resulting ketone 152 is then recovered and optionally purified by conventional methods such as precipitation, filtration, evaporation, crystallization, chromatography and the like. Alternatively, ketone 152 can be used in the next step without further purification and/or isolation.

Ketone 152 is then reacted with an appropriate aryl or heteroaryl-substituted alkyl halide 154, such as benzyl bromide. Typically, this can be accomplished by stirring the ketone 152 with an excess of potassium hydroxide and DMF and then adding at least an equimolar amount of the aryl or heteroaryl-substituted alkyl halide 154. The resulting ketone 156 is then recovered and optionally purified using conventional methods such as precipitation, filtration, evaporation, crystallization, chromatography and the like. Alternatively, ketone 156 can be used in the next step without further purification and/or isolation.

If L is —S(O)ᵣ— and r is two, then an appropriately substituted sulfonyl chloride may be used in place of alkyl halide 154.

Ketone 156 is then reduced to the corresponding alcohol 158 by conventional reducing agents such as sodium borohydride under conventional conditions.

Amine 162 is prepared from alcohol 156 with an excess, e.g., about 3 equivalents of a suitable amino protecting group, such as phthalimide. To the reaction is then added an excess of both triphenylphosphine and diisopropyl diazodicarboxylate (DIAD) while maintaining the reaction at a temperature of from about −20 to about 10° C. The reaction is allowed to warm to room temperature and continued until it is substantially complete, typically about 2 to about 24 h. The resulting protected amine (not shown) is then recovered and optionally purified by conventional methods such as precipitation, filtration, evaporation, crystallization, chromatography, and the like. Alternatively, the protected amine can be used directly in the next step without purification and/or isolation.

The protecting group is then removed by conventional techniques to provide for amine 162, which is then recovered and optionally purified by conventional methods such as precipitation, filtration, evaporation, crystallization, chromatography and the like. Alternatively, amine 162 can be used directly in the next step without purification and/or isolation.

Amine 162 is reacted under conventional reductive amination conditions described above with aldehyde 164 to provide for substituted amine 166 which is then recovered and optionally purified by conventional methods such as precipitation, filtration, evaporation, crystallization, chromatography and the like. Alternatively, substituted amine 166 can be used directly in the next step without purification and/or isolation.

Substituted amine 166 is then reacted under conventional amidation conditions with acyl chloride 168. Any protecting groups remaining on the resulting amide product can be removed by conventional methods and the product can be recovered and purified by conventional methods such as precipitation, filtration, evaporation, crystallization, chromatography and the like.

It will be well within the skill of the art to further modify the above preparation to synthesize other compounds of this invention.

D. Pharmaceutical Formulations

When employed as pharmaceuticals, the compounds of the subject invention are usually administered in the form of pharmaceutical compositions. These compositions can be administered by a variety of routes including oral, parenteral, transdermal, topical, rectal, and intranasal. These compounds are effective, for example, as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents;

and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, cancer in mammals, the compounds or pharmaceutical compositions thereof will be administered by any appropriate route, such as orally, topically, transdermally, and/or parenterally at a dosage to obtain and maintain a concentration, that is, an amount, or blood-level of active component in the mammal undergoing treatment that will be therapeutically effective. This is discussed in the next section in more detail.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
| --- | --- |
| Active Ingredient | 5.0 mg |
| Corn Oil | 1.0 mL |

FORMULATION EXAMPLE 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

An intravenous formulation may be prepared as follows:

| Ingredient | Quantity |
| --- | --- |
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mack Publishing Company, Philadelphia, Pa., 17th ed. (1985).

E. Dosage and Administration

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds of the instant invention are useful for inhibiting or treating a disorder mediated, at least in part, by the activity of KSP. In one aspect, the disorder that is mediated, at least in part by KSP, is a cellular proliferative disorder. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or mammalian subject in need of such treatment, comprising administering to the subject a therapeutically effective amount of a compound of formula I or II, either alone or in combination with other anticancer agents.

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas, sarcomas, and hematological malignancies.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound or composition of this invention may be administered to a mammal by a suitable route, such as orally, intravenously, parenterally, transdermally, topically, rectally, or intranasally.

Mammals include, for example, humans and other primates, pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 5 µg to about 50 mg per kilogram body weight per day, preferably about 1 mg to about 10 mg per kilogram body weight per day. In the alternative, for intravenous administration, the dose will typically be in the range of about 5 µg to about 50 mg per kilogram body weight, preferably about 500 µg to about 5000 µg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LC/MS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GC/MS analysis is performed on a Hewlett Packard instrument (HP6890 Series gas chromatograph with a Mass Selective Detector 5973; injector volume: 1 mL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, EtOAc, hexane, acetone, aqueous hydroxyamine and triethyl amine. Typical solvents employed for the reverse phase HPLC were varying concentrations of acetonitrile and water with 0.1% trifluoroacetic acid.

Unless otherwise stated all temperatures are in degrees Celsius. Also, in these examples and elsewhere, abbreviations have the following meanings:

Unless otherwise stated all temperatures are in degrees Celsius. Also, in these examples and elsewhere, abbreviations have the following meanings:

aq.=aqueous
ATP=adenosine triphosphate
boc=t-butoxy carbonyl
BSA=bovine serum albumin
DCM=dichloromethane
DIAD=diisopropyl diazodicarboxylate
DMAP=dimethylaminopyridine
DME=dimethoxy ethane
DMF=dimethylformamide
DMSO=dimethylsulfoxide
DTT=dithiothreitol
eq.=equivalence
$Et_3N$=triethyl amine
EtOAc=ethyl acetate
EtOH=ethanol
g=gram
h=hour
HPLC=high performance liquid chromatography
L=liter
M=molar
MeOH=methanol
mg=milligram
min=minute
mL=milliliter
mM=millimolar
mmol=millimole
mol=mole
N=normal
nm=nanometer
Ph=phenyl
$Ph_3P$=triphenyl phosphine
TBTU=N,N,N',N'-tetramethyl-O-(benzotraizol-1-yl)uronium tetrafluoroborate
THF=tetrahydrofuran
TMS=trimethyl silyl
μg=micrograms
μl=microliter
μM=micromolar Example 1

N-(3-Amino-propyl)-N-[1-(1-benzyl-5-methyl-1H-benzimidazol-2-yl)-2-methyl-propyl]-4-methyl-benzamide (compound 3)

Step 1. Benzyl-(4-methyl-2-nitro-phenyl)-amine

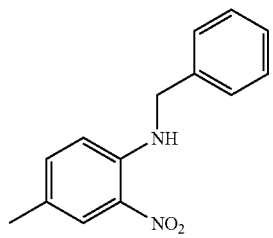

To a solution of 4-methyl-2-nitro-phenylamine (202 mg, 1.33 mmol) and benzaldehyde (0.68 mL, 6.65 mmol) in 5 mL dry dichloromethane at room temperature, was added sodium triacetoxyborohydride (282 mg, 1.33 mmol). Then acetic acid (76 μl, 1.33 mmol) was added. The reaction mixture was stirred at room temperature for 1 h. The solvent was evaporated and the solid was dissolved in ethyl acetate. The organic layer was washed with saturated $NaHCO_3$, dried over $MgSO_4$, filtered, and the solvent was removed in vacuo. The crude material was purified by flash chromatography to yield 300 mg (1.24 mmol, 94%) of benzyl-(4-methyl-2-nitro-phenyl)-amine.

Step 2. N1-Benzyl-4-methyl-benzene-1,2-diamine

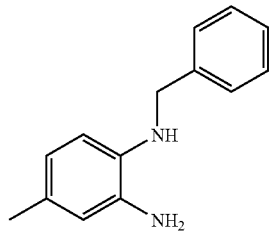

To a solution of benzyl-(4-methyl-2-nitro-phenyl)-amine (300 mg, 1.24 mmol) in 5 mL acetic acid, was added iron (300 mg, 1.24 mmol). The reaction mixture was heated to 40° C. under argon for 2 h. The mixture was cooled to ambient temperature and filtered through celite and the filtrate was concentrated. The resulting solid was dissolved in ethyl acetate. The organic layer was washed with saturated $NaHCO_3$, dried over $MgSO_4$, filtered and the filtrate was concentrated in vacuo to yield crude product that was used in step 3.

Step 3. [1-(2-Benzylamino-5-methyl-phenylcarbamoyl)-2-methyl-propyl]-carbamic acid tert-butyl ester

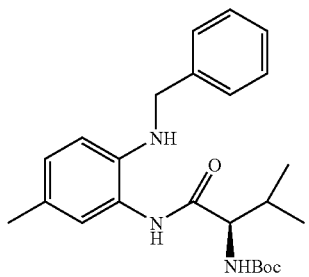

To a solution of N1-benzyl-4-methyl-benzene-1,2-diamine (1.24 mmol) and triethylamine (0.26 mL, 1.86 mmol) in dry DMF (5 mL), was added boc-D-valine (296 mg, 1.36 mmol) followed by TBTU (400 mg, 1.24 mmol). The reaction mixture was stirred at room temperature overnight. Ethyl acetate was added. The organic layer was washed with saturated NaHCO₃, dried over MgSO₄, filtered, and the filtrated was concentrated in vacuo. The crude material was purified by flash chromatography to yield [1-(2-Benzylamino-5-methyl-phenylcarbamoyl)-2-methyl-propyl]-carbamic acid tert-butyl ester.

Step 4. [1-(1-Benzyl-5-methyl-1H-benzimidazol-2-yl)-2-methyl-propyl]-carbamic acid tert-butyl ester

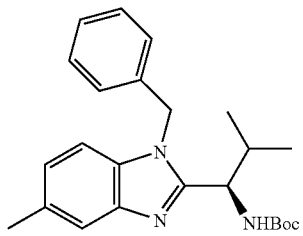

A solution of [1-(2-benzylamino-5-methyl-phenylcarbamoyl)-2-methyl-propyl]-carbamic acid tert-butyl ester (400 mg, 0.97 mmol) in acetic acid (4 mL) was heated at 100° C. for 2 h. The solvent was removed in vacuo and the resulting solid was dissolved in ethyl acetate. The organic layer was washed with saturated NaHCO₃, dried over MgSO₄, filtered and the filtrate was concentrated in vacuo. The crude product was purified by flash chromatography to give of [1-(1-benzyl-5-methyl-1H-benzimidazol-2-yl)-2-methyl-propyl]-carbamic acid tert-butyl ester (300 mg).

Step 5. 1-(1-Benzyl-5-methyl-1H-benzimidazol-2-yl)-2-methyl-propylamine

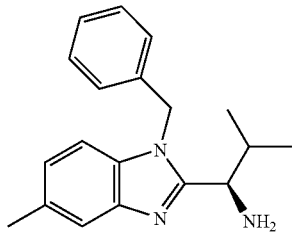

To a solution of 1-(1-benzyl-5-methyl-1H-benzimidazol-2-yl)-2-methyl-propylamine in DCM (2 mL), was added trifluoroacetic acid (0.5 mL). The reaction mixture was stirred at room temperature for 30 min. The solvent was removed in vacuo to give the free amine product.

Step 6a. 3-(1,3-Dioxo-1,3-dihydro-isoindol-2-yl)-propionaldehyde

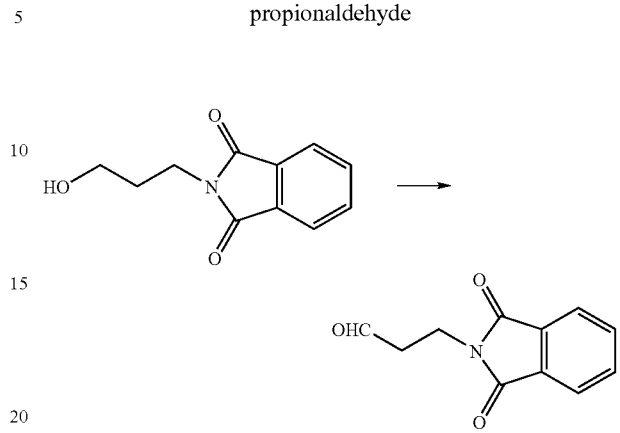

The reaction was carried out with oven dried glassware. DMSO (85 µl, 1.1 mmol) was added to oxalyl chloride solution (0.35 mL 2 M DCM solution with 5 mL dry DCM) at −78° C. The reaction mixture was stirred at −78° C. for 10 min. 2-(3-Hydroxy-propyl)-isoindole-1,3-dione solution (102 mg, 0.5 mmol, in 2 mL DCM) was added drop wise in 2 min. Then triethylamine (0.35 mL, 2.5 mmol) was added drop wise in 2 min. The mixture was stirred for additional 30 minutes at −78° C. and was warmed up to room temperature. The reaction mixture was extracted with ethyl acetate. The organic layer was washed with saturated sodium bicarbonate, dried over MgSO₄, filtered, and the filtrated was concentrated in vacuo. The crude product was purified by flash chromatography to give 3-(1,3-dioxo-1,3-dihydro-isoindol-2-yl)-propionaldehyde.

Step 6b. 2-{3-[1-(1-Benzyl-5-methyl-1H-benzimidazol-2-yl)-2-methyl-propylamino]-propyl}-isoindole-1,3-dione

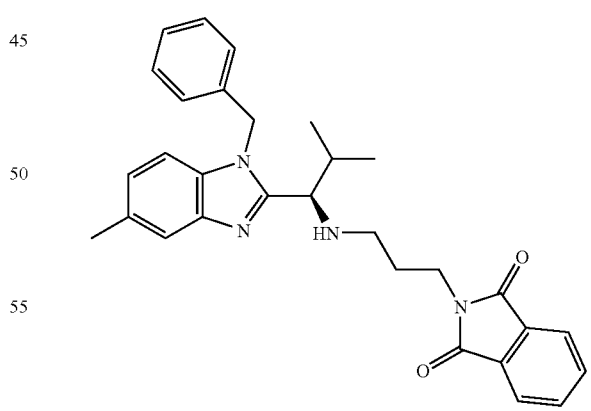

To a solution of 1-(1-benzyl-5-methyl-1H-benzimidazol-2-yl)-2-methyl-propylamine (0.56 mmol) and 3-(1,3-dioxo-1,3-dihydro-isoindol-2-yl)-propionaldehyde (114 mg, 0.56 mmol) in dry DCM (3 mL) at room temperature, was added sodium triacetoxyborohydride (119 mg, 0.56 mmol). After 10 min., acetic acid (34 µl, 0.56 mmol) was added to the reaction mixture. The mixture was stirred at room temperature for 1 h.

The solvent was removed in vacuo and the solid was dissolved in ethyl acetate. The organic layer was washed with saturated NaHCO₃, dried over MgSO₄, filtered and the filtrate was concentrated in vacuo. The crude product was purified by flash chromatography to give crude material that was used in step 7.

Step 7. N-[1-(1-Benzyl-5-methyl-1H-benzimidazol-2-yl)-2-methyl-propyl]-N-[3-(1,3-dioxo-1,3-dihydro-isoindol-2-yl)-propyl]-4-methyl-benzamide

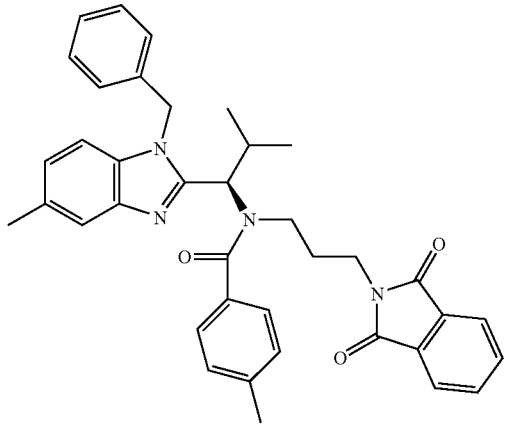

To a solution of 2-{3-[1-(1-benzyl-5-methyl-1H-benzimidazol-2-yl)-2-methyl-propylamino]-propyl}-isoindole-1,3-dione (0.56 mmol) and triethylamine (0.58 mL, 3.36 mmol) in DCM (3 mL) at 0° C., was added p-toluoyl chloride (0.38 mL, 2.8 mmol). The reaction mixture was stirred at 0° C. for 30 min. Ethyl acetate and saturated sodium bicarbonate were added. The mixture was extracted with ethyl acetate. The organic layers was combined, dried over MgSO₄, filtered, and the filtrate was concentrated in vacuo. The crude material was purified by flash chromatography to give N-[1-(1-benzyl-5-methyl-1H-benzimidazol-2-yl)-2-methyl-propyl]-N-[3-(1,3-dioxo-1,3-dihydro-isoindol-2-yl)-propyl]-4-methyl-benzamide (181 mg).

Step 8. N-(3-Amino-propyl)-N-[1-(1-benzyl-5-methyl-1H-benzimidazol-2-yl)-2-methyl-propyl]-4-methyl-benzamide

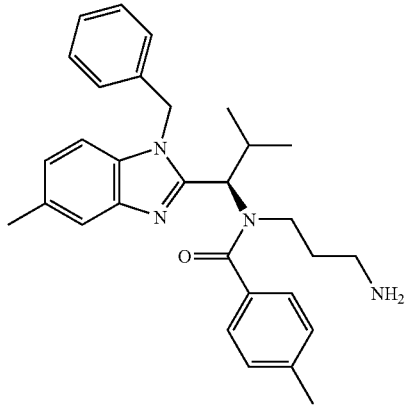

To a solution of N-[1-(1-benzyl-5-methyl-1H-benzimidazol-2-yl)-2-methyl-propyl]-N-[3-(1,3-dioxo-1,3-dihydro-isoindol-2-yl)-propyl]-4-methyl-benzamide (0.302 mmol) in ethanol at room temperature, was added hydrazine (0.19 mL, 6 mmol). The reaction was stirred at room temperature for 1 h. The crude product was purified via reverse phase chromatography to give N-(3-amino-propyl)-N-[1-(1-benzyl-5-methyl-1H-benzimidazol-2-yl)-2-methyl-propyl]-4-methyl-benzamide (129 mg).

Example 2

N-(3-Amino-propyl)-N-[1-(1-benzyl-5-vinyl-1H-benzimidazol-2-yl)-2-methyl-propyl]-4-methyl-benzamide

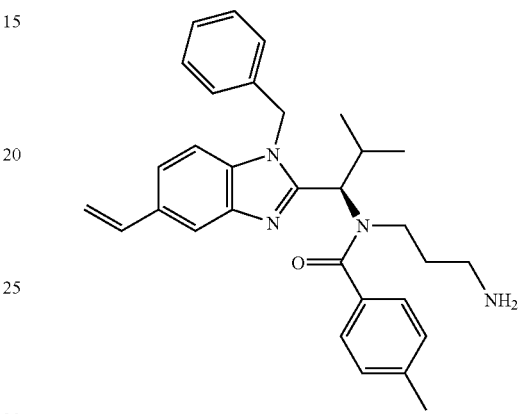

Step 1. [1-(1-Benzyl-5-vinyl-1H-benzimidazol-2-yl)-2-methyl-propyl]-carbamic acid tert-butyl ester

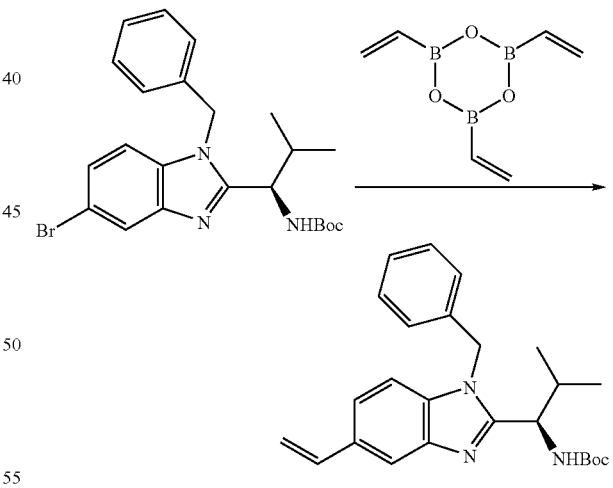

To a solution of [1-(1-benzyl-5-bromo-1H-benzimidazol-2-yl)-2-methyl-propyl]-carbamic acid tert-butyl ester (this compound was obtained starting from 4-bromo-2-nitro-phenylamine following steps 1-4 in Example 1) (58 mg, 0.127 mmol) in DME (2 mL) solution, was added tetrakis(triphenylphosphine)palladium(0) (9 mg, 0.008 mmol). The mixture was stirred at room temperature under argon for 10 min. Then potassium carbonate (18 mg, 0.127 mmol), water (0.6 mL) and 2,4,6-trivinyl-cyclotriboroxane pyridine complex (48 mg, 0.127 mmol) was added to the reaction mixture. The mixture was heated at 110° C. under argon for 1 h and then was cooled down to room temperature. Ethyl acetate and saturated sodium bicarbonate solution were added. The mixture was extracted with ethyl acetate. The organic layers was dried over MgSO$_4$, filtered, and the solvent was removed in vacuo. The residue was subjected to flash chromatograph to give [1-(1-benzyl-5-vinyl-1H-benzimidazol-2-yl)-2-methyl-propyl]-carbamic acid tert-butyl ester (43 mg).

N-(3-Amino-propyl)-N-[1-(1-benzyl-5-vinyl-1H-benzimidazol-2-yl)-2-methyl-propyl]-4-methyl-benzamide was synthesized from the preceding compound following the step 5 to step 8 in Example 1, using methylhydrazine instead of hydrazine.

Example 3

N-(3-Amino-propyl)-N-[1-(1-benzyl-5-ethynyl-1H-benzimidazol-2-yl)-2-methyl-propyl]-4-methyl-benzamide (Compound 22)

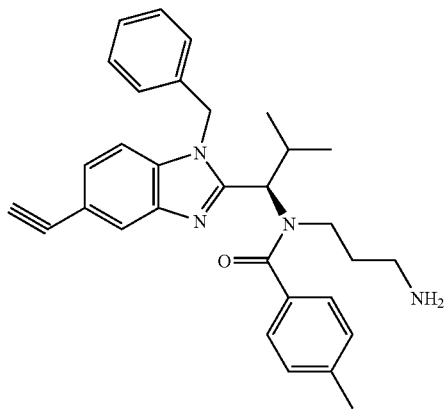

Step 1. [1-(1-Benzyl-5-trimethylsilanylethynyl-1H-benzimidazol-2-yl)-2-methyl-propyl]-carbamic acid tert-butyl ester

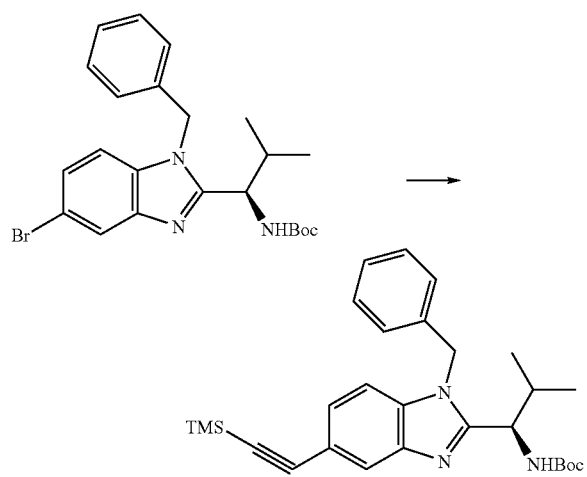

To a solution of [1-(1-benzyl-5-bromo-1H-benzimidazol-2-yl)-2-methyl-propyl]-carbamic acid tert-butyl ester (this compound was obtained starting from 4-bromo-2-nitro-phenylamine following steps 1-4 in Example 1) (48 mg, 0.105 mmol) in dioxane (3 mL) in a microwave reaction tube, was added tetrakis(triphenylphosphine)palladium(0) (12 mg, 0.01 mmol), copper (I) iodide (2 mg, 0.01 mmol), ethynyl-trimethyl-silane (22 μl, 0.16 mmol), and triethylamine (0.4 mL). The mixture was purged argon for 5 min. and then heated to 120° C. in microwave reactor for 10 min. The reaction was cooled down to room temperature. Ethyl acetate and saturated sodium bicarbonate were added. The mixture was extracted with ethyl acetate. The organic layer was dried over MgSO$_4$, filtered, and the solvent was removed in vacuo. The residue was subjected to flash chromatograph to give [1-(1-benzyl-5-trimethylsilanylethynyl-1H-benzimidazol-2-yl)-2-methyl-propyl]-carbamic acid tert-butyl ester (20 mg).

Step 2. [1-(1-Benzyl-5-ethynyl-1H-benzimidazol-2-yl)-2-methyl-propyl]-carbamic acid tert-butyl ester

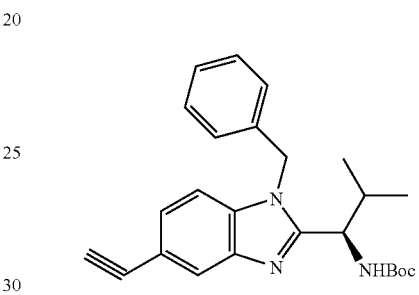

To a solution of [1-(1-benzyl-5-trimethylsilanylethynyl-1H-benzimidazol-2-yl)-2-methyl-propyl]-carbamic acid tert-butyl ester (20 mg, 0.042 mmol) in 2 mL THF at room temperature, was added 0.2 mL tetrabutylammonium fluoride solution (0.2 mL of 1 N in THF solution). The reaction mixture was stirred at room temperature for 15 min. The solvent was removed under vacuum and the residue was dissolved in a mixture of ethyl acetate and saturated sodium bicarbonate. The mixture was extracted with ethyl acetate. The organic layers was dried over MgSO$_4$, filtered, and the solvent was removed in vacuo. The crude was used in next synthesis directly.

N-(3-Amino-propyl)-N-[1-(1-benzyl-5-ethynyl-1H-benzimidazol-2-yl)-2-methyl-propyl]-4-methyl-benzamide was synthesized using the preceding compound following the step 5 to step 8 in Example 1, using methylhydrazine instead of hydrazine.

Example 4

N-(3-aminopropyl)-N-[1-(1-benzyl-5-chloro-1H-indol-2-yl)-2-methylpropyl]benzamide (Compound 45)

Step 1. 1-phenylsulfonyl-5-chloroindole

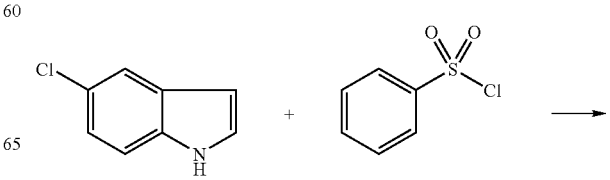

-continued

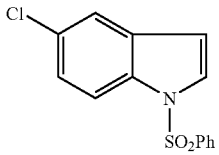

To a stirred solution of 5-chloroindole (20 g, 131.93 mmol, 1 eq.) in dry DMF (250 mL) at 0° C., was added NaH (5.38 g, 134.57 mmol, 1.02 eq.). After stirring at room temperature for 1 h, benzenesulfonyl chloride (23.77 g, 134.57 mmol, 1.02 eq.) was added slowly. The reaction mixture was stirred for additional 1 h, then poured into 1 L of 5% aq. NaHCO$_3$ and extracted with EtOAc (×3). The organic layers were combined, washed with H$_2$O (×3), brine (×3), dried over (Na$_2$SO$_4$), filtered, and the filtrate was concentrated. The material was purified by flash chromatography to yield 30 g of 1-phenylsulfonyl-5-chloroindole as colorless crystals.

Step 2. 1-(5-chloro-1-phenylsulfonylindole)-2-methylpropan-1-ol

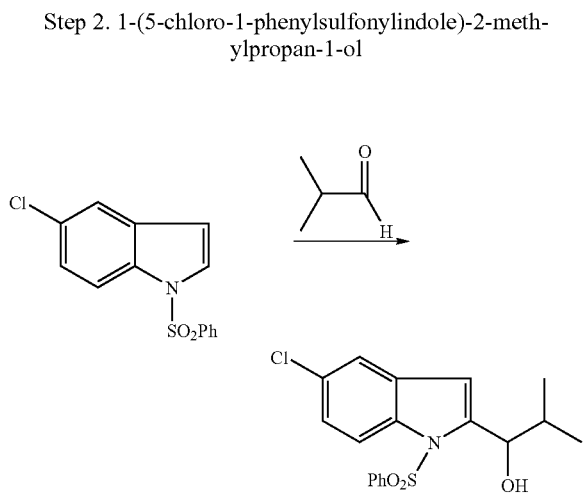

To a solution of 1-phenylsulfonyl-5-chloroindole (6.8 mmol) in dry THF (20 mL) at −78° C., was added n-butyl lithium (10.2 mmol) drop wise (about 30 min). After stirring for 10 min., the mixture was warmed up to −20° C. It was then cooled to −78° C., a solution of isobutylaldehyde (10.2 mmol) in 5 mL of dry THF was added slowly. After warming up to room temperature overnight, the mixture was poured into water, then extracted with EtOAc (×3). The organic layers were combined, washed with H$_2$O (×3), brine (×3), dried over (Na$_2$SO$_4$), filtered, and the filtrate was concentrated. The material was purified by flash chromatography (20% EtOAc: hexane) to yield 2.4 g of 1-(5-chloro-1-phenylsulfonylindole)-2-methylpropan-1-ol.

Step 3. 1-(5-Chloro-1-phenylsulfonylindole)-2-methylpropan-1-one

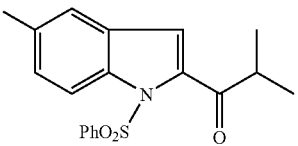

To a solution of 1-(5-chloro-1-phenylsulfonylindole)-2-methylpropan-1-ol (700 mg) in 35 mL of chloroform was added MnO$_2$ (6.7 g). The mixture was stirred at room temperature overnight, filtered over celite and the filtrate was concentrated. The crude material was purified by flash chromatography (30% EtOAc:hexane) to yield 1-(5-chloro-1-phenylsulfonylindole)-2-methylpropan-1-one as colorless oil.

Step 4. 1-(5-chloro-1H-indole-2-yl)-2-methylpropan-1-one

To a solution of ethanol (20 mL) and 10% aq. NaOH (10 mL), was added 1-(5-chloro-1-phenylsulfonylindole)-2-methylpropan-1-one (290 mg). The mixture was heated under reflux for 2 h. After cooling, the solution was poured into water, and extracted with EtOAc (×3). The organic layers were combined, washed with H$_2$O (×3), brine (×3), dried over (Na$_2$SO$_4$), filtered, and the filtrate was concentrated to give 227 mg of 1-(5-chloro-1H-indole-2-yl)-2-methylpropan-1-one.

Step 5. 1-(1-benzyl-5-chloro-1H-indole-2-yl)-2-methylpropan-1-one

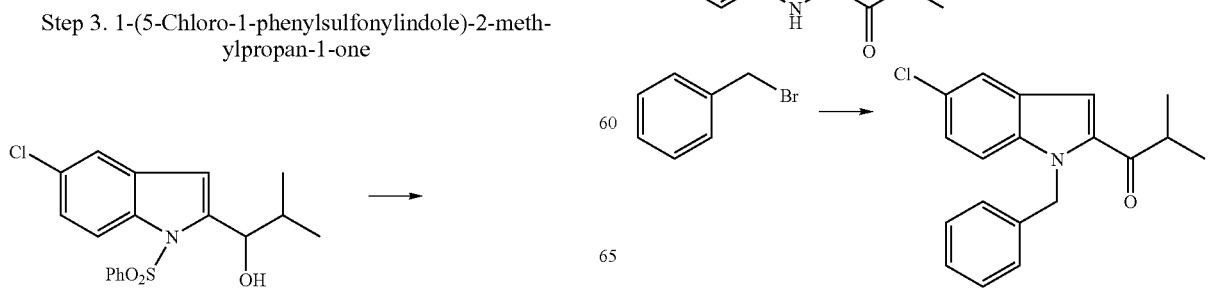

To a solution of 1-(5-chloro-1H-indole-2-yl)-2-methylpropan-1-one (1 mmol) in 15 mL of DMF, was added KOH (2 mmol) at 0° C. The mixture was stirred for 30 min., followed by adding benzyl bromide (2 mmol) slowly. The mixture was warmed up to room temperature and stirred for additional 1 h. The solution was poured into water, and extracted with EtOAc (×3). The organic layers were combined, washed with H$_2$O (×3), brine (×3), dried (Na$_2$SO$_4$), filtered, and the filtrate was concentrated. The material was purified by flash chromatography (10% EtOAc:hexane) to yield 1-(1-benzyl-5-chloro-1H-indole-2-yl)-2-methylpropan-1-one.

Step 6. 1-(1-benzyl-5-chloro-1H-indole-2-yl)-2-methylpropan-1-ol

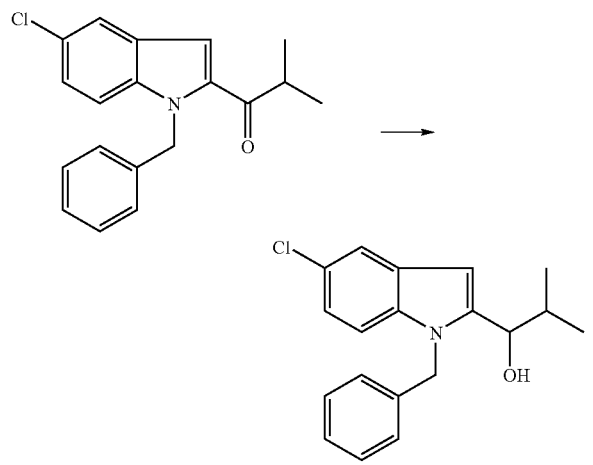

To a solution of 1-(1-benzyl-5-chloro-1H-indole-2-yl)-2-methylpropan-1-one (0.6 mmol) in 5 mL of MeOH, was added NaBH$_4$ (1.8 mmol) at 0° C. The mixture was stirred for additional 30 min. The solution was poured into ice water, and extracted with EtOAc (×3). The organic layers were combined, washed with H$_2$O (×3), brine (×3), dried over Na$_2$SO$_4$, filtered, and the filtrate was concentrated to yield 182 mg of 1-(1-benzyl-5-chloro-1H-indole-2-yl)-2-methylpropan-1-ol.

Step 7. 2-(1-(1-Benzyl-5-chloro-1H-indol-2-yl)-2-methylpropyl)isoindoline-1,3-dione

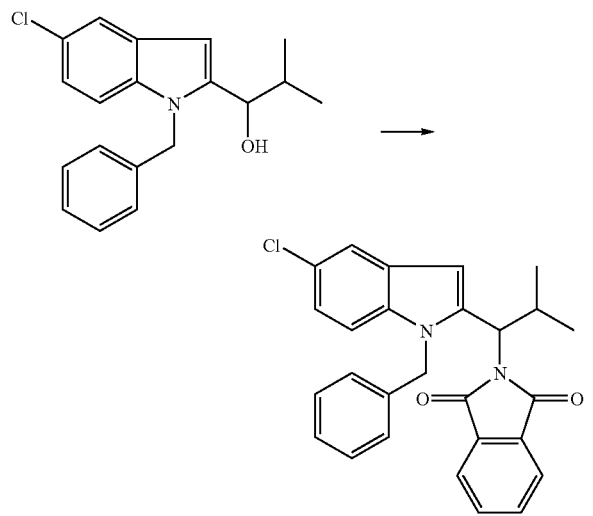

To a solution of 1-(1-benzyl-5-chloro-1H-indole-2-yl)-2-methylpropan-1-ol (0.6 mmol), Ph$_3$P, (1 mmol), phthalimide (1.8 mmol) in 5 mL of dry THF at 0° C., was added DIAD (1 mmol) drop wise. The mixture was warmed up to room temperature gradually and stirred overnight. The solution was poured into water, and extracted with EtOAc (×3). The organic layers were combined, washed with H$_2$O (×3), brine (×3), dried (Na$_2$SO$_4$), filtered, and the filtrate was concentrated. The material was purified by flash chromatography (10% EtOAc:hexane) to yield 170 mg of title compound.

Step 8. 1-(1-benzyl-5-chloro-1H-indole-2-yl)-2-methylpropan-1-amine

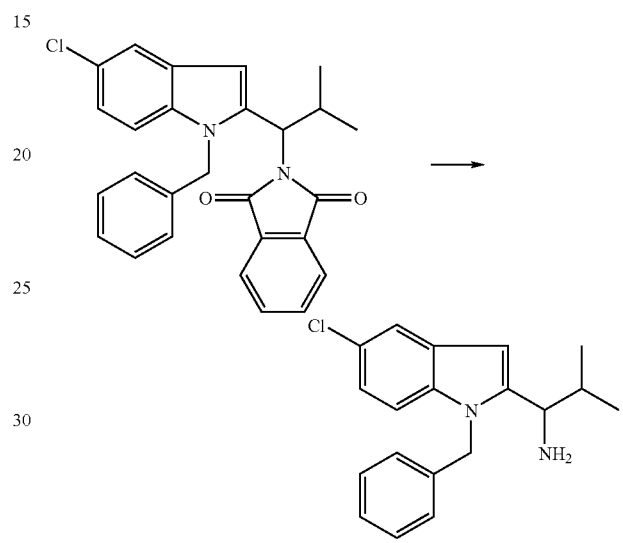

To a solution of product of step 7 (0.4 mmol) in 10 mL of EtOH, was added hydrazine (4 mmol) at 0° C. The mixture was stirred at 80° C. overnight. The solution was poured into water, and extracted with EtOAc (×3). The organic layers were combined, washed with 10% NaOH, H$_2$O (×3), brine (×3), dried (Na$_2$SO$_4$), filtered, and the filtrate was concentrated. The material was purified by flash chromatography (20% EtOAc:hexane) to yield 52 mg of 1-(1-benzyl-5-chloro-1H-indole-2-yl)-2-methylpropan-1-amine.

Step 9

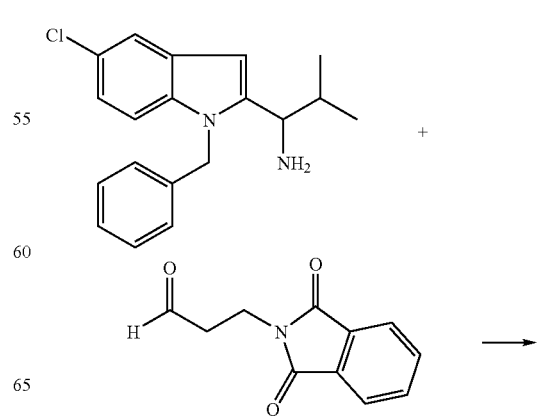

-continued

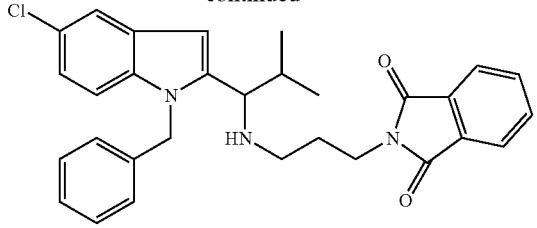

To a solution of 1-(1-benzyl-5-chloro-1H-indole-2-yl)-2-methylpropan-1-amine (0.44 mmol) in 10 mL of anhydrous DCM, was added aldehyde (0.44 mmol) and sodium triacetoxyborohydride (0.44 mmol) at 0° C. The mixture was stirred at room temperature overnight. The solution was poured into 10% aq. NaOH, and extracted with EtOAc (×3). The organic layers were combined, washed with H₂O (×3), brine (×3), dried (Na₂SO₄), filtered, and the filtrate was concentrated. The material was purified by flash chromatography (20% EtOAc:hexane) to yield 40 mg of title compound.

Step 10. N-(1-(1-benzyl-5-chloro-1H-indol-2-yl)-2-methylpropyl)-N-(3-(1,3-dioxoisoindolin-2-yl)propyl)benzamide

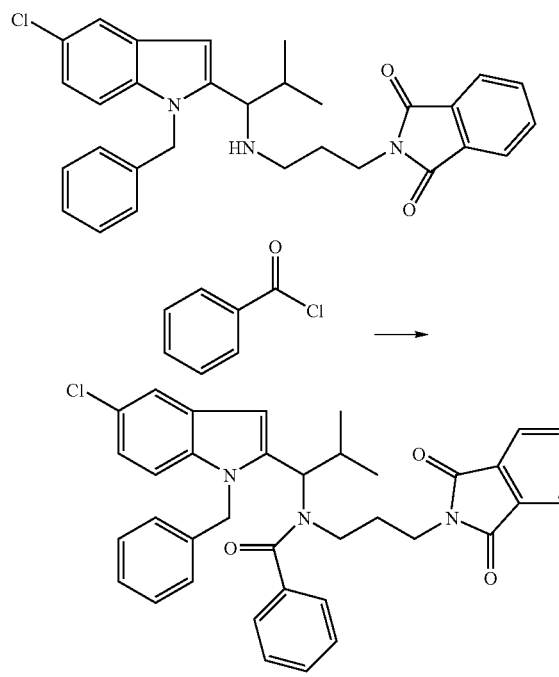

To a solution of product of step 9 (0.1 mmol) in 2 mL of anhydrous DCM at 0° C., was added DMAP (0.01 mmol), Et₃N (0.4 mmol), and p-toluoyl chloride (0.4 mmol). The mixture was stirred at room temperature for 1 h. The solution was poured into water, and extracted with EtOAc (×3). The organic layers were combined, washed with H₂O (×3), brine (×3), dried (Na₂SO₄), filtered, and the filtrate was concentrated. The material was purified by flash chromatography (10% EtOAc:hexane) to yield 50 mg of title compound.

Step 11. N-(3-aminopropyl)-N-[1-(1-benzyl-5-chloro-1H-indol-2-yl)-2-methylpropyl]benzamide

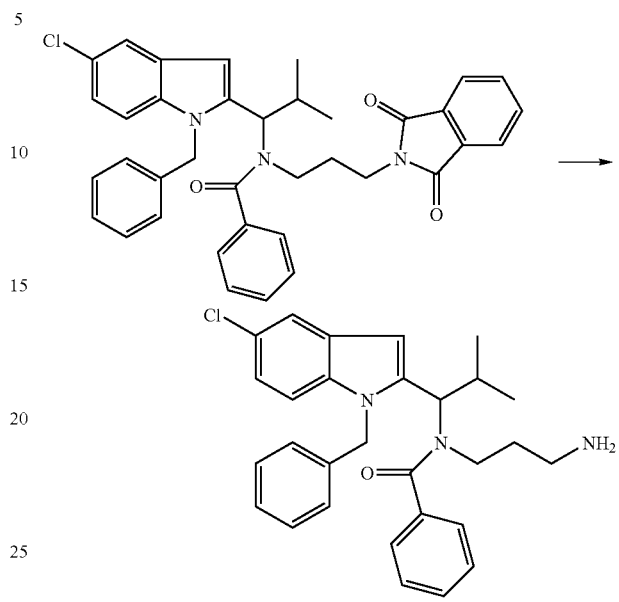

To a solution of product of step 10 (50 mg) in 1 mL of EtOH was added hydrazine (0.1 mL). The mixture was stirred at room temperature for 2 h. The solution was poured into water, and extracted with EtOAc (×3). The organic layers were combined, washed with 10% NaOH aq., H₂O (×3), brine (×3), dried (Na₂SO₄), filtered, and the filtrate was concentrated. The material was purified preparatory HPLC to give N-(3-aminopropyl)-N-[1-(1-benzyl-5-chloro-1H-indol-2-yl)-2-methylpropyl]benzamide.

Example 5

N-(3-aminopropyl)-N-[1-(1-benzyl-5-chloro-1H-indol-2-yl)-2-methylpropyl]-4-methylbenzamide (Compound 46)

The title compound was synthesized using similar procedure as in Example 4 using p-toluoyl chloride in place of benzoyl chloride in step 10 of Example 4.

Example 6

N-(3-aminopropyl)-N-{1-[5-chloro-1-(phenylsulfonyl)-1H-indol-2-yl]-2-methylpropyl}-4-methylbenzamide (Compound 47)

The title compound was synthesized using similar procedure as in Example 4 using 1-(5-chloro-1-phenylsulfonylindole)-2-methylpropan-1-ol (product of step 2 of example 4) in place of 1-(1-benzyl-5-chloro-1H-indole-2-yl)-2-methylpropan-1-ol in step 7 of example 4.

The compounds in the table below may be prepared using the methodology described in the previous Examples and Methods. The following tables also include compounds described in the experimental section. The starting materials used in the synthesis were recognizable to one of skill in the art and were commercially available or were prepared using known methods. The compounds were named using ACD/Name Batch Version 5.04 (Advanced Chemistry Development Inc.; Toronto, Ontario; www.acdlabs.com).

TABLE 3

| Compound | Structure | MH+ | Name |
|---|---|---|---|
| 1 | Chiral | 475.3 | N-(3-aminopropyl)-N-[(1R)-1-(1-benzyl-1H-benzimidazol-2-yl)-2-methylpropyl]-4-chlorobenzamide |
| 2 | Chiral | 455.2 | N-(3-aminopropyl)-N-[(1R)-1-(1-benzyl-1H-benzimidazol-2-yl)-2-methylpropyl]-4-methylbenzamide |
| 3 | Chiral | 468.64 | N-(3-aminopropyl)-N-[(1R)-1-(1-benzyl-5-methyl-1H-benzimidazol-2-yl)-2-methylpropyl]-4-methylbenzamide |

TABLE 3-continued

| Compound | Structure | MH+ | Name |
|---|---|---|---|
| 4 | Chiral | 489.06 | N-(3-aminopropyl)-N-[(1R)-1-(1-benzyl-5-chloro-1H-benzimidazol-2-yl)-2-methylpropyl]-4-methylbenzamide |
| 5 | Chiral | 507.1 | N-(3-aminopropyl)-N-{(1R)-1-[1-(4-chlorobenzyl)-6-fluoro-1H-benzimidazol-2-yl]-2-methylpropyl}-4-methylbenzamide |
| 6 | Chiral | 475.3 | N-(3-aminopropyl)-N-[(1R)-1-(1-benzyl-5-chloro-1H-benzimidazol-2-yl)propyl]-4-methylbenzamide |

TABLE 3-continued

| Compound | Structure | MH+ | Name |
|---|---|---|---|
| 7 | Chiral | 521.0 | N-(3-aminopropyl)-N-[(1R)-1-(1-benzyl-1H-benzimidazol-2-yl)-2-methylpropyl]-4-bromobenzamide |
| 8 | Chiral | 535.3 | N-(3-aminopropyl)-N-[(1R)-1-(1-benzyl-5-bromo-1H-benzimidazol-2-yl)-2-methylpropyl]-4-methylbenzamide |
| 9 | Chiral | 505.0 | N-(3-aminopropyl)-N-[(1R)-1-(1-benzyl-5-bromo-1H-benzimidazol-2-yl)propyl]benzamide |

TABLE 3-continued

| Compound | Structure | MH+ | Name |
|---|---|---|---|
| 10 | Chiral | 519.1 | N-(3-aminopropyl)-N-[(1R)-1-(1-benzyl-5-bromo-1H-benzimidazol-2-yl)propyl]-4-methylbenzamide |
| 11 | Chiral | 485.4 | N-(3-aminopropyl)-N-{(1R)-1-[1-(3-hydroxybenzyl)-5-methyl-1H-benzimidazol-2-yl]-2-methylpropyl}-4-methylbenzamide |
| 12 | Chiral | 487.2 | N-(3-aminopropyl)-N-{(1R)-1-[1-(3-fluorobenzyl)-5-methyl-1H-benzimidazol-2-yl]-2-methylpropyl}-4-methylbenzamide |

TABLE 3-continued

| Compound | Structure | MH+ | Name |
|---|---|---|---|
| 13 | Chiral | 483.2 | N-(3-aminopropyl)-N-[(1R)-1-(1-benzyl-5-ethyl-1H-benzimidazol-2-yl)-2-methylpropyl]-4-methylbenzamide |
| 14 | Chiral | 499.2 | N-(3-aminopropyl)-N-{(1R)-1-[5-ethyl-1-(3-hydroxybenzyl)-1H-benzimidazol-2-yl]-2-methylpropyl}-4-methylbenzamide |
| 15 | Chiral | 501.2 | N-(3-aminopropyl)-N-{(1R)-1-[5-ethyl-1-(3-fluorobenzyl)-1H-benzimidazol-2-yl]-2-methylpropyl}-4-methylbenzamide |

TABLE 3-continued

| Compound | Structure | MH+ | Name |
|---|---|---|---|
| 16 | Chiral | 535.1 | N-1-[(1R)-1-(1-benzyl-5-bromo-1H-benzimidazol-2-yl)-2-methylpropyl]-N-1-(4-methylbenzyl)-beta-alaninamide |
| 17 | Chiral | 481.2 | N-(3-aminopropyl)-N-[(1R)-1-(1-benzyl-5-vinyl-1H-benzimidazol-2-yl)-2-methylpropyl]-4-methylbenzamide |
| 18 | Chiral | 485.2 | N-(3-aminopropyl)-N-[(1R)-1-(1-benzyl-5-methoxy-1H-benzimidazol-2-yl)-2-methylpropyl]-4-methylbenzamide |

TABLE 3-continued

| Compound | Structure | | MH+ | Name |
|---|---|---|---|---|
| 19 | 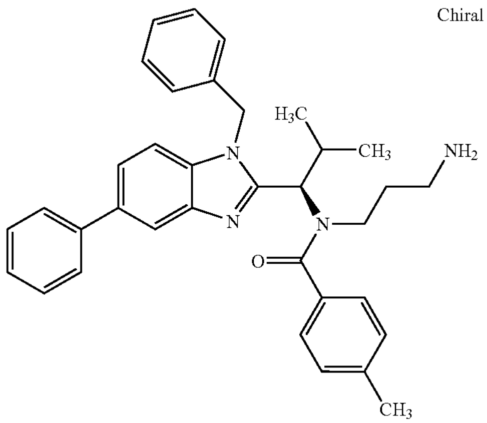 | Chiral | 531.2 | N-(3-aminopropyl)-N-[(1R)-1-(1-benzyl-5-phenyl-1H-benzimidazol-2-yl)-2-methylpropyl]-4-methylbenzamide |
| 20 | 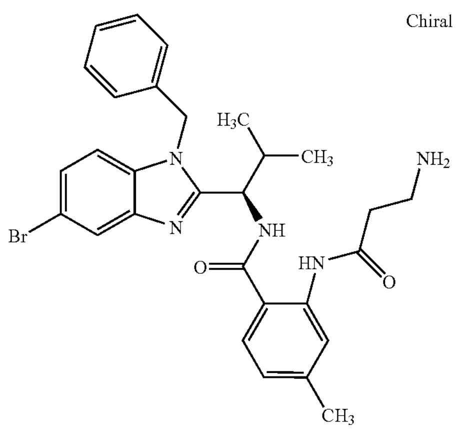 | Chiral | 564.1 | 2-(beta-alanylamino)-N-[(1R)-1-(1-benzyl-5-bromo-1H-benzimidazol-2-yl)-2-methylpropyl]-4-methylbenzamide |
| 21 | 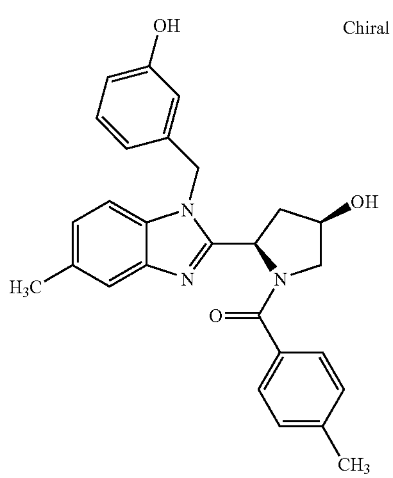 | Chiral | 442.2 | (3R,5R)-5-[1-(3-hydroxybenzyl)-5-methyl-1H-benzimidazol-2-yl]-1-(4-methylbenzoyl)pyrrolidin-3-ol |

TABLE 3-continued

| Compound | Structure | | MH+ | Name |
|---|---|---|---|---|
| 22 | 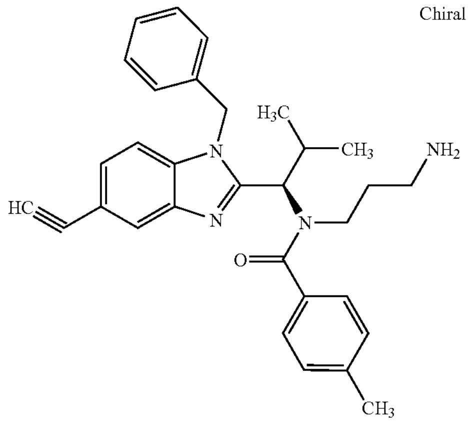 | Chiral | 479.2 | N-(3-aminopropyl)-N-[(1R)-1-(1-benzyl-5-ethynyl-1H-benzimidazol-2-yl)-2-methylpropyl]-4-methylbenzamide |
| 23 | 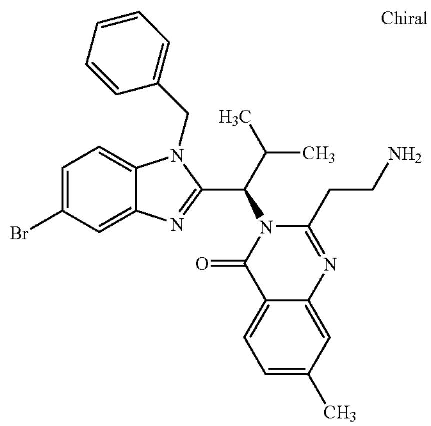 | Chiral | 546.1 | 2-(2-aminoethyl)-3-[(1R)-1-(1-benzyl-5-bromo-1H-benzimidazol-2-yl)-2-methylpropyl]-7-methylquinazolin-4(3H)-one |
| 24 | 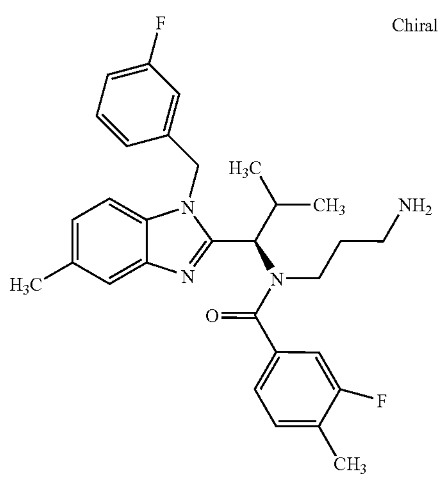 | Chiral | 505.2 | N-(3-aminopropyl)-3-fluoro-N-{(1R)-1-[1-(3-fluorobenzyl)-5-methyl-1H-benzimidazol-2-yl]-2-methylpropyl}-4-methylbenzamide |

TABLE 3-continued

| Compound | Structure | | MH+ | Name |
|---|---|---|---|---|
| 25 | 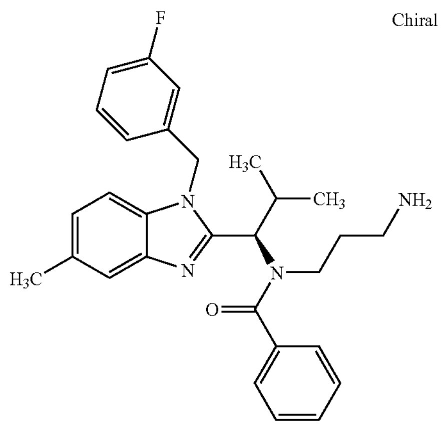 | Chiral | 473.2 | N-(3-aminopropyl)-N-{(1R)-1-[1-(3-fluorobenzyl)-5-methyl-1H-benzimidazol-2-yl]-2-methylpropyl}benzamide |
| 26 | 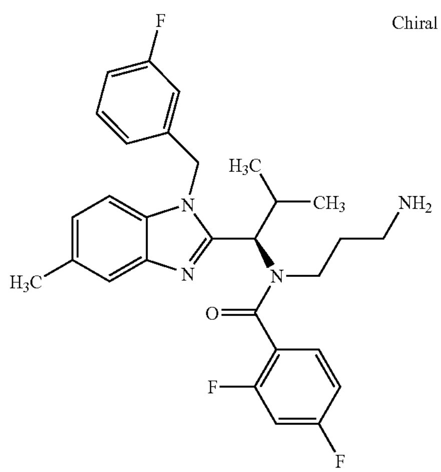 | Chiral | 509.1 | N-(3-aminopropyl)-2,4-difluoro-N-{(1R)-1-[1-(3-fluorobenzyl)-5-methyl-1H-benzimidazol-2-yl]-2-methylpropyl}benzamide |
| 27 | 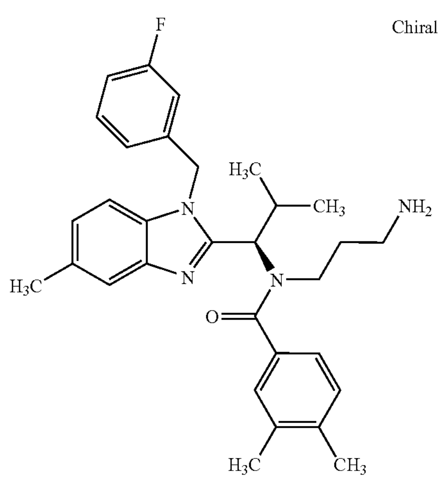 | Chiral | 501.1 | N-(3-aminopropyl)-N-{(1R)-1-[1-(3-fluorobenzyl)-5-methyl-1H-benzimidazol-2-yl]-2-methylpropyl}-3,4-dimethylbenzamide |

TABLE 3-continued

| Compound | Structure | MH+ | Name |
|---|---|---|---|
| 28 | Chiral | 590.0 | N-((1R)-1-{1-[3-(acetylamino)benzyl]-5-bromo-1H-benzimidazol-2-yl}-2-methylpropyl)-N-(3-aminopropyl)-4-methylbenzamide |
| 29 | Chiral | 509.1 | N-(3-aminopropyl)-2,6-difluoro-N-{(1R)-1-[1-(3-fluorobenzyl)-5-methyl-1H-benzimidazol-2-yl]-2-methylpropyl}benzamide |
| 30 | Chiral | 491.2 | N-(3-aminopropyl)-2-fluoro-N-{(1R)-1-[1-(3-fluorobenzyl)-5-methyl-1H-benzimidazol-2-yl]-2-methylpropyl}benzamide |

TABLE 3-continued
| Compound | Structure | MH+ | Name |
|---|---|---|---|
| 31 | 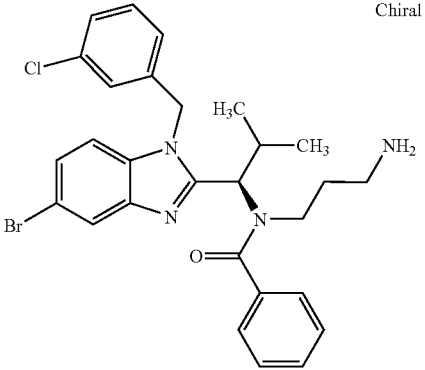 Chiral | 553.0 | N-(3-aminopropyl)-N-{(1R)-1-[5-bromo-1-(3-chlorobenzyl)-1H-benzimidazol-2-yl]-2-methylpropyl}benzamide |
| 32 | 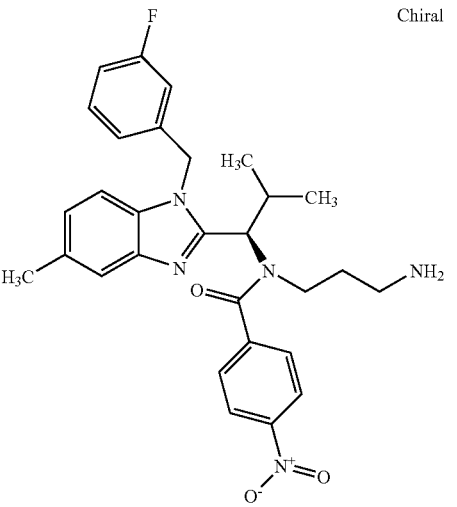 Chiral | 518.2 | N-(3-aminopropyl)-N-{(1R)-1-[1-(3-fluorobenzyl)-5-methyl-1H-benzimidazol-2-yl]-2-methylpropyl}-4-nitrobenzamide |
| 33 | 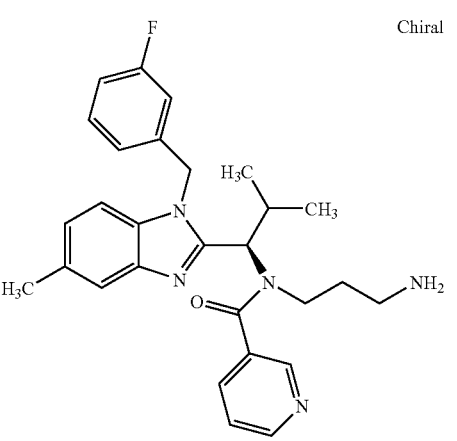 Chiral | 474.2 | N-(3-aminopropyl)-N-{(1R)-1-[1-(3-fluorobenzyl)-5-methyl-1H-benzimidazol-2-yl]-2-methylpropyl}nicotinamide |

TABLE 3-continued

| Compound | Structure | MH+ | Name |
|---|---|---|---|
| 34 | Chiral | 474.2 | N-(3-aminopropyl)-N-{(1R)-1-[1-(3-fluorobenzyl)-5-methyl-1H-benzimidazol-2-yl]-2-methylpropyl}isonicotinamide |
| 35 | Chiral | 523.2 | N-(3-aminopropyl)-N-{(1R)-1-[1-(3-fluorobenzyl)-5-methyl-1H-benzimidazol-2-yl]-2-methylpropyl}-2-naphthamide |
| 36 | Chiral | 487.2 | N-(3-aminopropyl)-N-{(1R)-1-[1-(3-fluorobenzyl)-5-methyl-1H-benzimidazol-2-yl]-2,2-dimethylpropyl}benzamide |

TABLE 3-continued

| Compound | MH+ | Name |
|---|---|---|
| 37 | 489.2 | N-(3-aminopropyl)-N-{(1R)-1-[1-(3-fluorobenzyl)-5-methyl-1H-benzimidazol-2-yl]-2-methylpropyl}-4-hydroxybenzamide |
| 38 | 579.2 | N-[3-(benzylamino)propyl]-N-[(1R)-1-(1-benzyl-5-chloro-1H-benzimidazol-2-yl)-2-methylpropyl]-4-methylbenzamide |
| 39 | 585.3 | N-[(1R)-1-(1-benzyl-5-chloro-1H-benzimidazol-2-yl)-2-methylpropyl]-N-{3-[(cyclohexylmethyl)amino]propyl}-4-methylbenzamide |

TABLE 3-continued

| Compound | Structure | | MH+ | Name |
|---|---|---|---|---|
| 40 | 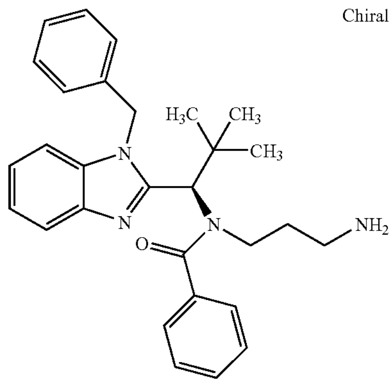 | Chiral | 455.2 | N-(3-aminopropyl)-N-[(1R)-1-(1-benzyl-1H-benzimidazol-2-yl)-2,2-dimethylpropyl]benzamide |
| 41 | 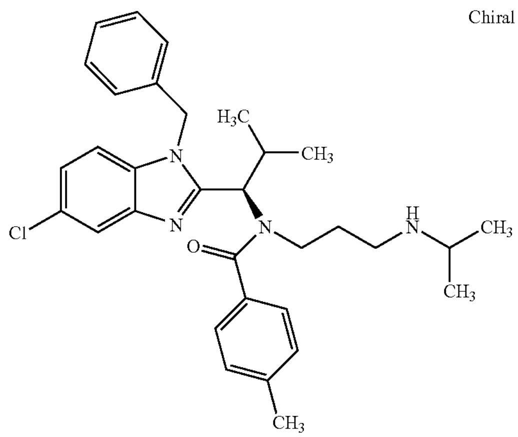 | Chiral | 531.2 | N-[(1R)-1-(1-benzyl-5-chloro-1H-benzimidazol-2-yl)-2-methylpropyl]-N-[3-(isopropylamino)propyl]-4-methylbenzamide |
| 42 | 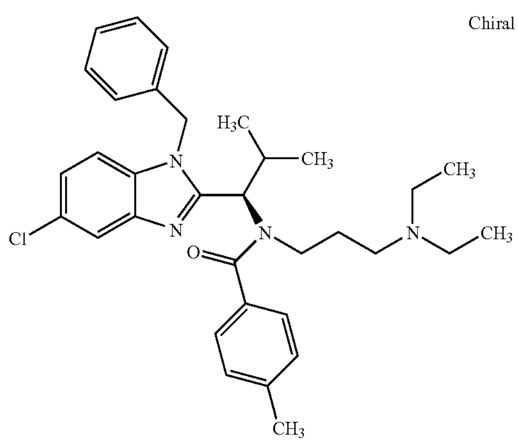 | Chiral | 545.16 | N-[(1R)-1-(1-benzyl-5-chloro-1H-benzimidazol-2-yl)-2-methylpropyl]-N-[3-(diethylamino)propyl]-4-methylbenzamide |

TABLE 3-continued

| Compound | Structure | MH+ | Name |
|---|---|---|---|
| 43 | Chiral | 543.2 | N-[(1R)-1-(1-benzyl-5-chloro-1H-benzimidazol-2-yl)-2-methylpropyl]-N-[3-(cyclobutylamino)propyl]-4-methylbenzamide |
| 44 | Chiral | 557.0 | N-(3-aminopropyl)-N-{(1R)-1-[5-bromo-1-(3,5-difluorobenzyl)-1H-benzimidazol-2-yl]-2-methylpropyl}benzamide |
| 45 | 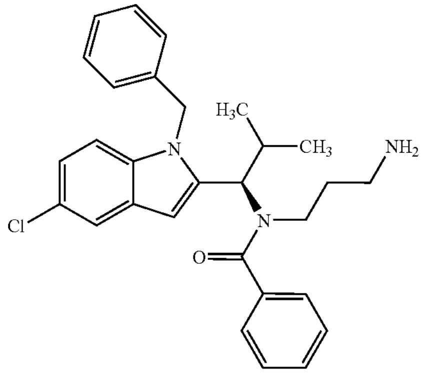 | 474.1 | N-(3-aminopropyl)-N-[1-(1-benzyl-5-chloro-1H-indol-2-yl)-2-methylpropyl]benzamide |

TABLE 3-continued

| Compound | Structure | MH+ | Name |
|---|---|---|---|
| 46 | 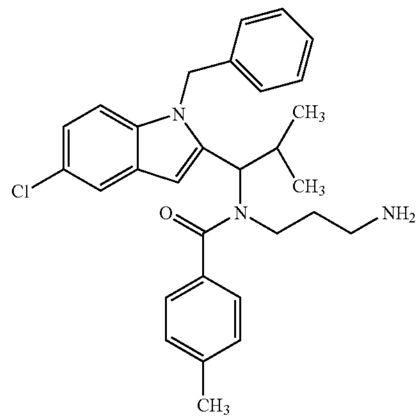 | 488.2 | N-(3-aminopropyl)-N-[1-(1-benzyl-5-chloro-1H-indol-2-yl)-2-methylpropyl]-4-methylbenzamide |
| 47 | 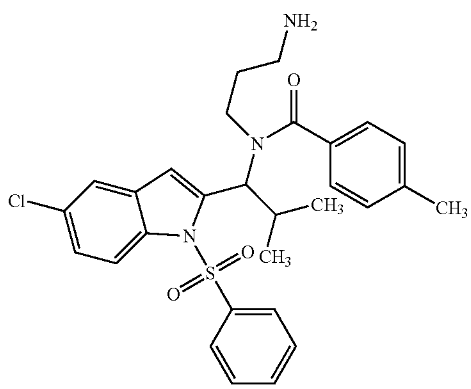 | 538.1 | N-(3-aminopropyl)-N-{1-[5-chloro-1-(phenylsulfonyl)-1H-indol-2-yl]-2-methylpropyl}-4-methylbenzamide |
| 48 | Chiral | 557.1 | N-{3-[(aminocarbonyl)(cyano)amino]propyl}-N-[(1R)-1-(1-benzyl-5-chloro-1H-benzimidazol-2-yl)-2-methylpropyl]-4-methylbenzamide |

TABLE 3-continued

| Compound | Structure | | MH+ | Name |
|---|---|---|---|---|
| 49 | (structure) | Chiral | 532.1 | N-{3-[(aminocarbonyl)amino]propyl}-N-[(1R)-1-(1-benzyl-5-chloro-1H-benzimidazol-2-yl)-2-methylpropyl]-4-methylbenzamide |
| 50 | (structure) | Chiral | 496.2 | N-{(1R)-1-[1-(3-fluorobenzyl)-5-methyl-1H-benzimidazol-2-yl]-2-methylpropyl}-N-(1H-imidazol-4-ylmethyl)benzamide |

Example 7

Assay for Determining KSP Activity

This example provides a representative in vitro assay for determining KSP activity in vitro. Purified microtubules obtained from bovine brain were purchased from Cytoskeleton Inc. (Denver, Colo., USA). The motor domain of human KSP (Eg5, KNSL1) was cloned, expressed, and purified to greater than 95% homogeneity. Biomol Green was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM $MgCl_2$, 10 mM DTT and 0.25 mg/mL BSA) to a final concentration of 35 μg/mL microtubules and 45 nM KSP. The microtubule/KSP mixture was then pre-incubated at 37° C. for 10 min to promote the binding of KSP to microtubules.

To each well of the testing plate (384-well plate) containing 1.25 μL of inhibitor or test compound in DMSO (or DMSO only in the case of controls) were added 25 μL of ATP solution (ATP diluted to a concentration of 300 μM in assay buffer) and 25 μL of the above-described microtubule/KSP solution. The plates were incubated at room temperature for 1 h. Following incubation, 65 μL of Biomol Green (a malachite green-based dye that detects the release of inorganic phosphate) was added to each well. The plates were incubated for an additional 5 to 10 min then the absorbance at 630 nm was determined using a Victor II plate reader. The amount of absorbance at 630 nm corresponded to the amount of KSP activity in the samples. The $IC_{50}$ of each inhibitor or test compound was then determined based on the decrease in absorbance at 630 nm at each concentration, via nonlinear regression using either XLFit for Excel or Prism data analysis software by GraphPad Software Inc.

Preferred compounds of the invention have a biological activity as measured by an $IC_{50}$ of less than about 1 mM in assay protocols described in Example 7 above, with preferred embodiments having biological activity of less than about 25 μM, with particularly preferred embodiments having biological activity of less than about 1000 nM, and with the most preferred embodiments having biological activity of less than about 100 nM.

Example 8

Inhibition of Cellular Proliferation in Tumor Cell Lines Treated with KSP Inhibitors Cells are plated in 96-well plates at densities of about 500 cells per well of a 96-well plate and are allowed to grow for 24 hours. The cells are then treated with various concentrations of compounds for 72 hours. Then, 100 μl of CellTiter Glo is added. CellTiter Glo is a tetrazolium-based assay using the reagent 3-(4,5-dimethylthiazol-2-yl) 5-(3-carboxymethoxyphenyl)-2-(4-sulfophenyl)-2H-tetrazolium (MTS) (U.S. Pat. No. 5,185,450) (see Promega product catalog #G3580, CellTiter 96 Aqueous One Solution Cell Proliferation Assay). The cells are then incubated in the dark for 30 minutes. The amount of luminescence is determined for each well using a Walloc Trilux plate reader, which correlates with the number of cells per well. The number of viable cells in the wells that receive only DMSO (0.5%) serve as an indication of 0% inhibition, while wells without cells serve as 100% inhibition of cell growth. The compound concentration that resulted in a 50% growth inhibition ($GI_{50}$) is determined graphically from sigmoidal dose-response curves of log-transformed dose values versus cell counts (percent of control) at 72 hours of continuous compound exposure.

The cell lines used are listed below.

The cell proliferation assay is performed as described above.

Cancer Cell Lines
Colo 205—colon carcinoma
  RPMI 1640+10% FBS+1% L-glutamine+1% P/S+1% NaPyr.+Hepes
  +4.5 g/L Glucose+1% NaBicarb.
MDA 435—breast cancer—high met
  EMEM+10% FBS+1% P/S+1% L-Glutamine+1% NEAA+1% NaPyr+1% vitamins
HCT-15 and HCT116—colon carcinoma
  RPMI 1640+10% FBS+1% L-glutamine+1% P/S
Drug Resistant Cell Lines
KB3.1—colon epidermal carcinoma; parental cell line
  Iscove's+10% FBS+1% L-glutamine+1% P/S
KBV1—p-glycoprotein associated multi-drug resistant cell line
  RPMI 1640+10% FBS+1% L-glutamine+1% P/S+0.2 ug/ml Vinblastine
KB85—p-glycoprotein associated multi-drug resistant cell line
  DMEM+10% FBS+1% L-glutamine+1% P/S+10 ng/ml Colchicine Preferred compounds of the invention have a biological activity as measured by an $GI_{50}$ of less than about 1 mM in assay protocols described with some embodiments having biological activity of less than about 25 µM, with other embodiments having biological activity of less than about 1000 nM, and with still other embodiment having a $GI_{50}$ of less than about 100 nM.

Example 9

Clonogenic Softagar Assay Protocol

Human cancer cells are plated at a density of $3 \times 10^5$ cells per well in a 6-well plate. The next day, a compound of interest at a certain concentration is added to each well. After 24 and 48 hours of incubation, the cells are harvested, washed and counted. The following steps are performed using the Multimek 96 robot. Then, 500 viable cells per well are plated in a 96-well plate that is coated with PolyHema to prevent attachment of the cells to the bottom of the well. Agarose (3% stock) is melted, diluted in warmed media and added to the cells to a final concentration of 0.5%. After the soft agar solidified, the plates are incubated at 37° C. for 6 days. Alamar blue dye is added to cells and plates are incubated for an additional 6 hours. The optical density change is measured on a Tecan plate reader and is considered to correlate with the number of colonies formed in soft agar. A cancerous cell is able to grow on the agar and thus will show an increase in optical density. A reading of decreased optical density means that the cancer cells are being inhibited. It is contemplated that compounds of this invention will exhibit a decrease in optical density.

We claim:
1. A compound of formula IC:

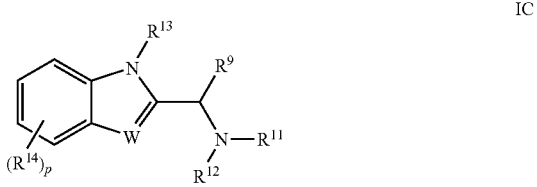

IC wherein
W is =CH— or =N—;
p is equal to 0, 1, 2 or 3;
$R^9$ is alkyl or substituted alkyl;
$R^{11}$ is —$X^1$-$A^2$, wherein $X^1$ is —C(O)— and $A^2$ is selected from the group consisting of alkyl, substituted alkyl, aryl, substituted aryl, heteroaryl, and substituted heteroaryl;
$R^{12}$ is selected from the group consisting of -alkylene-amino, -alkylene-substituted amino, -alkylene-aryl, -alkylene-substituted aryl, -alkylene-nitrogen containing heterocyclic, -alkylene-heteroaryl, and -alkylene-substituted heteroaryl wherein the alkylene is optionally substituted;
or $R^9$ and $R^{12}$ together with the carbon atom attached to $R^9$ and the nitrogen atom attached to $R^{12}$ form a group selected from the group consisting of heterocyclic, substituted heterocyclic, heteroaryl, and substituted heteroaryl;
$R^{13}$ is -$L^1$-$A^3$, wherein $L^1$ is —S(O)$_r$— where r is 1 or 2 or $C_1$ to $C_2$ straight chain alkylene, and $A^3$ is selected from the group consisting of aryl optionally substituted with 1-2 groups independently selected from the group consisting of hydroxy, alkyl, halo, and acylamino, heteroaryl, and substituted heteroaryl;
each $R^{14}$ is independently selected from the group consisting of halo, $C_2$ to $C_3$ alkynyl, $C_2$ to $C_3$ alkenyl, $C_1$ to $C_5$ alkyl optionally substituted with halo, $C_1$ to $C_3$ alkoxy, and phenyl;
or a pharmaceutically acceptable salt or ester thereof.

2. The compound of claim 1, wherein $R^9$ is selected from the group consisting of ethyl, isopropyl, and t-butyl.

3. The compound of claim 1, wherein $A^2$ is aryl or heteroaryl optionally substituted with a substituent selected from the group consisting of halo, alkyl, acylamino, nitro, and hydroxy.

4. The compound of claim 1, wherein $R^{11}$ is selected from the group consisting of (2-chloro-6-methylpyridin-4-yl)carbonyl; (5-methylimidazol-4-yl)carbonyl; (dimethylamino)methyl carbonyl; (naphth-2-yl)carbonyl; (pyridin-3-yl)carbonyl; (pyridin-4-yl)carbonyl; 1,5-dimethylpyrazol-3-ylcarbonyl; 1-methyl-5-trifluoromethylpyrazol-4-ylcarbonyl; 1-methyl-5-chloropyrazol-4-ylcarbonyl; 2-(2-aminoethylamido)-4-methylbenzoyl; 2,4-difluorobenzoyl; 2,4-dimethylthiazol-5-ylcarbonyl; 2,6-difluorobenzoyl; 2-aminoethylcarbonyl; 2-aminothiazol-4-ylcarbonyl; 2-chlorobenzoyl; 2-chloropyridin-5-ylcarbonyl; 2-fluorobenzoyl; 2methoxybenzoyl; 2-methylpyridin-5-ylcarbonyl; 3,4-dichlorobenzoyl; 3,4-dimethylbenzoyl; 3-chlorobenzoyl; 3-fluoro-4-methylbenzoyl; 3-hydroxypyridin-4-ylcarbonyl; 4-aminopyridin-3-ylcarbonyl; 4-bromobenzoyl;

4-chlorobenzoyl; 4-chloropyridin-3-ylcarbonyl; 4-dimethylaminobenzoyl; 4-hydroxybenzoyl; 4-hydroxypyridin-3-ylcarbonyl; 4-methoxybenzoyl; 4-methyl-2-(aminoethylcarbonylamino)benzoyl; 4-methylbenzoyl; 4-methylisoxazol-3-ylcarbonyl; 4-methylpyridin-3-ylcarbonyl; 4-morpholino-N-ylpyridin-3-ylcarbonyl; 4-nitrobenzoyl; 4-t-butylbenzoyl; 4-trifluoromethylbenzoyl; 4-trifluoromethylpyridin-3-ylcarbonyl; 5-chloropyridin-3-ylcarbonyl; 5-methylpyrazol-3-ylcarbonyl; 6-chloropyridin-3-ylcarbonyl; benzoyl; cyclohexylcarbonyl; furan-3-ylcarbonyl; isoxazol-3-ylcarbonyl; piperidin-4-ylcarbonyl; pyrazin-2-ylcarbonyl; pyridazin-3-ylcarbonyl; pyridazin-4-ylcarbonyl; tetrahydrofuran-2-ylcarbonyl; tetrahydrofuran-3-ylcarbonyl; and thiazol-4-ylcarbonyl.

5. The compound of claim 1, wherein $R^{11}$ is selected from the group consisting of:

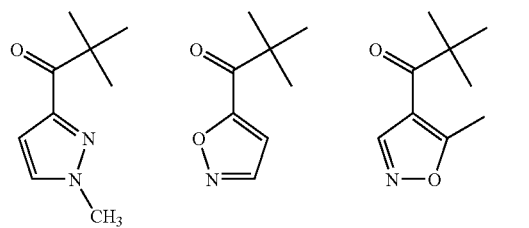

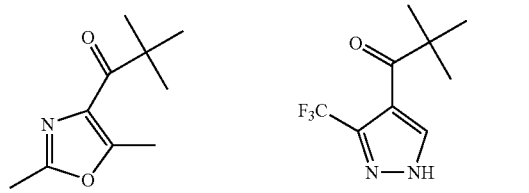

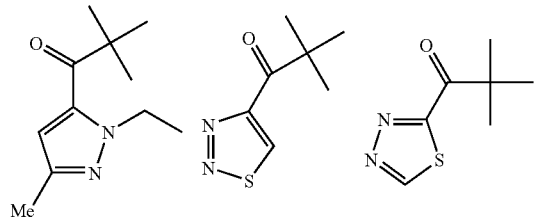

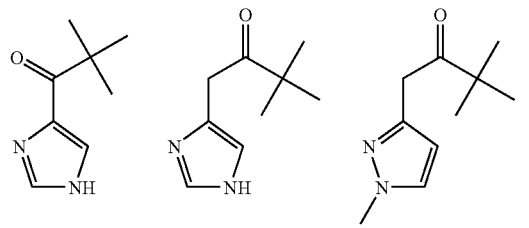

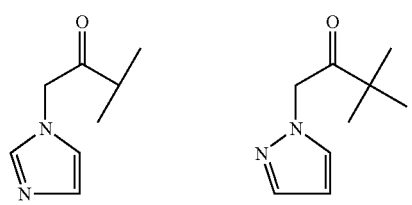

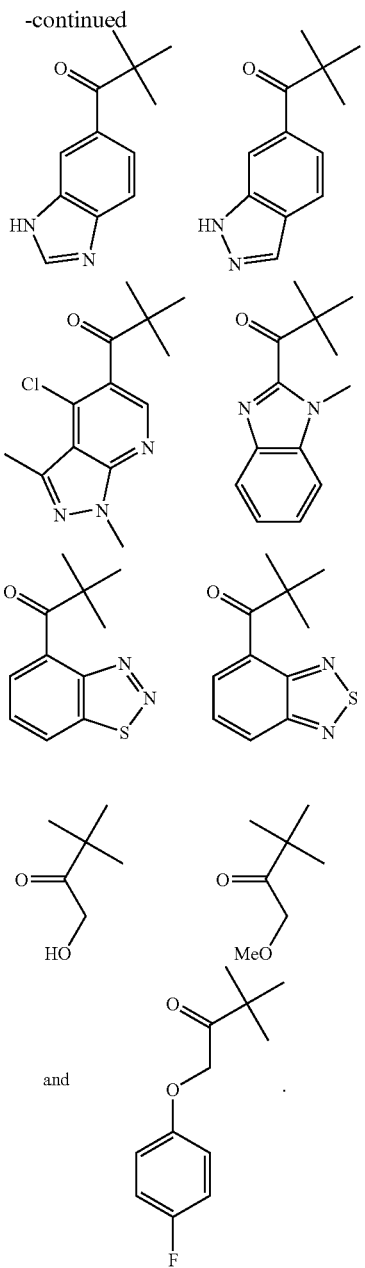

6. The compound of claim 4, wherein $R^{11}$ is selected from the group consisting of 2-aminoethylcarbonyl; 4-methyl-2-(aminoethylcarbonylamino)benzoyl; (naphth-2-yl)carbonyl; (pyridin-3-yl)carbonyl; (pyridin-4-yl)carbonyl; 2-(2-aminoethylamido)-4-methylbenzoyl; 2,4-difluorobenzoyl; 2,6-difluorobenzoyl; 2-fluorobenzoyl; 3,4-dimethylbenzoyl; 3-fluoro-4-methylbenzoyl; 4-bromobenzoyl; 4-chlorobenzoyl; 4-hydroxybenzoyl; 4-methylbenzoyl; 4-nitrobenzoyl; and benzoyl.

7. The compound of claim 1, wherein $R^9$ and $R^{12}$, together with the carbon atom attached to $R^9$ and the nitrogen atom attached to $R^{12}$ form a heterocyclic or substituted heterocyclic group.

8. The compound of claim 7, wherein the substituted heterocyclic group is 3-hydroxy-pyrrolidinyl.

9. The compound of claim 1, wherein $R^{12}$ is selected from the group consisting of (aminomethylcarbonyl)aminoethyl; 2,2-dimethyl-3-(4-methylpiperazin-1-yl)propyl; 2,2-dimethyl-3-dimethylaminopropyl; 2-aminoethyl; 2-hydroxyethyl-3-aminopropyl; 2-hydroxypyridin-4-ylmethyl; 2-hydroxypyridin-5-ylmethyl; 3-(1-cyanourea)propyl; 3-(benzylamino)propyl; 3-(cyclobutylamino)propyl; 3-(cyclohexylmethylamino)propyl; 3-(diethylamino)propyl; 3-(isopropylamino)propyl; 3-[(3-trifluoromethylpyridin-6-yl)amino]propyl; 3-[(5-pyridin-3-yloxyindazol-3-yl)methylamino]propyl; 3-[(6-fluoroindazol-3-yl)methylamino]propyl; 3-[(aminomethyl-carbonyl)amino]propyl; 3-[5-cyanopyridin-2-yl]propyl; 3-[[5-(pyridin-3-yloxy)indazol-3-yl]methylamino]propyl; 3-amino-3-(aminopropyl-methyl)propyl; 3-aminopropyl; 3-methylsulfonylaminopropyl; 3-ureapropyl; 5-methoxyindazol-3-ylmethyl; piperidin-3-ylmethyl; and pyrrolidin-2-ylmethyl.

10. The compound of claim 1, wherein $R^{12}$ is selected from the group consisting of:

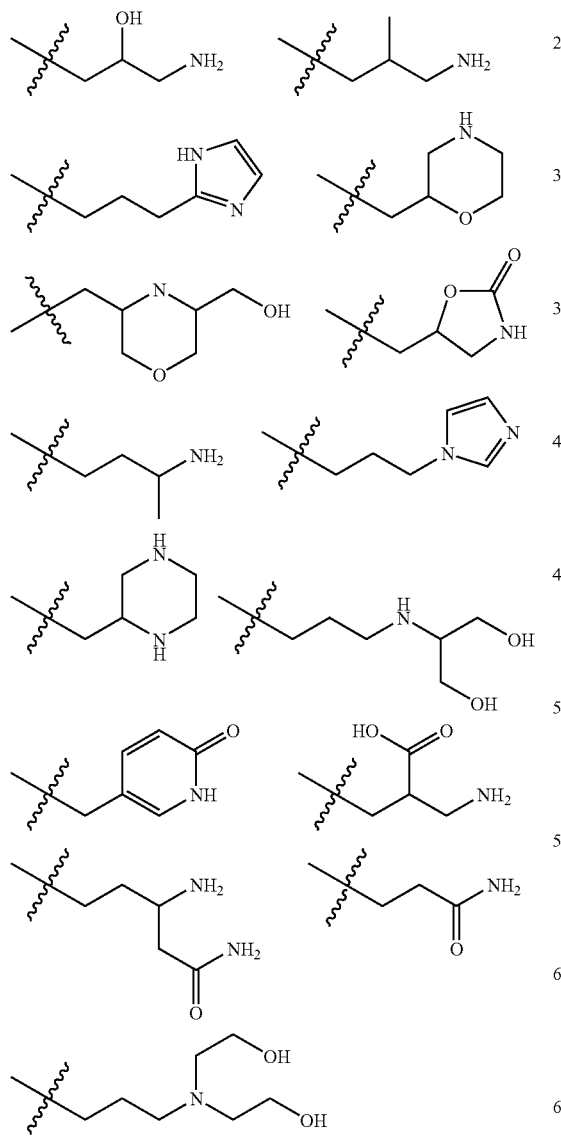

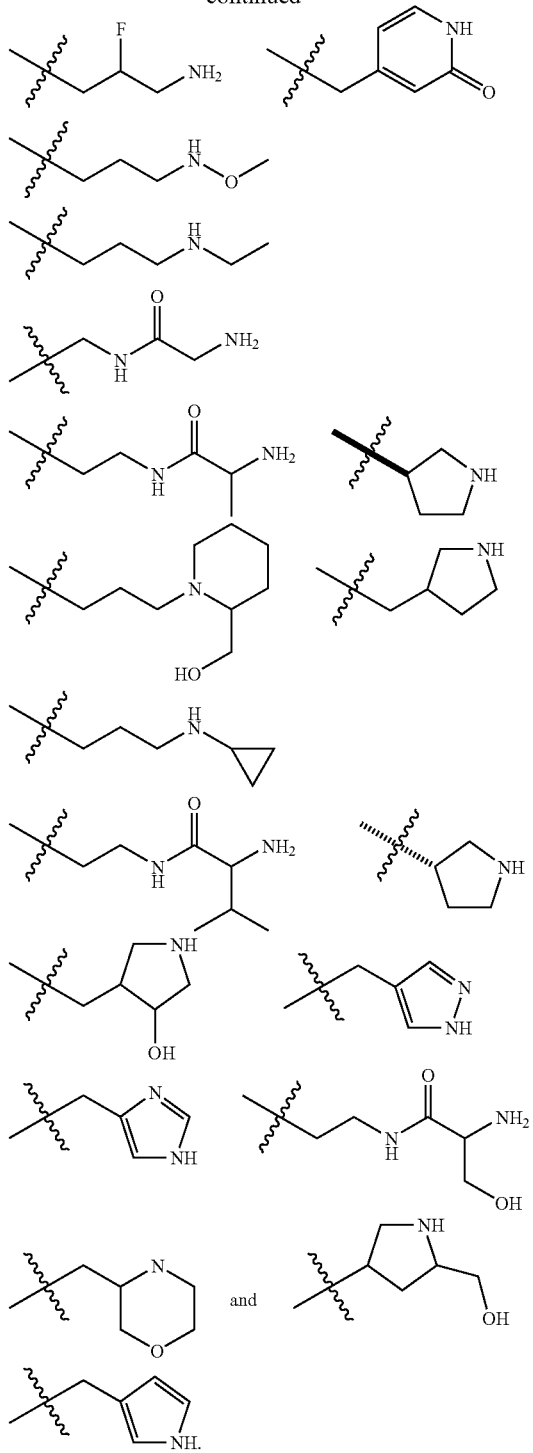

11. The compound of claim 1, wherein $R^{12}$ is selected from the group consisting of 3-(1-cyanourea)propyl; 3-(benzylamino)propyl; 3-(cyclobutylamino)propyl; 3-(cyclohexylmethylamino)propyl; 3-(diethylamino)propyl; 3-(isopropylamino)propyl; 3-aminopropyl; 3-ureapropyl; 4-methylbenzyl; and imidazol-4-ylmethyl.

12. The compound of claim 1, wherein $L^1$ is —SO$_2$— or —CH$_2$— and $A^3$ is optionally substituted aryl.

13. The compound of claim 1, wherein $R^{13}$ is selected from the group consisting of 2,4-difluorobenzyl; 2-methylbenzyl; 3-(methylamido)benzyl; 3,5-difluorobenzyl; 3-chlorobenzyl; 3-fluorobenzyl; 3-hydroxybenzyl; 3-methylbenzyl; 4-chlorobenzyl; 4-methylbenzyl; benzyl; and thiazol-4-ylmethyl.

14. The compound of claim 1, wherein $R^{13}$ groups are selected from the group consisting of: 3-(methylamido)benzyl; 3,5-difluorobenzyl; 3-chlorobenzyl; 3-fluorobenzyl; 3-hydroxybenzyl; 4-chlorobenzyl; and benzyl.

15. The compound of claim 1, wherein p is 1.

16. The compound of claim 15, wherein $R^{14}$ is selected from the group consisting of: propargyl; bromo; —$CF_3$; chloro; ethyl; ethynyl; fluoro; methoxy; methyl; phenyl; and vinyl.

17. The compound of claim 1, wherein $R^{14}$ is selected from the group consisting of bromo; chloro; ethyl; methoxy; methyl; propargyl; vinyl; fluoro; and phenyl.

18. The compound of claim 1, wherein p is 0.

19. A compound selected from the group consisting of:
N-(3-aminopropyl)-N-[(1R)-1-(1-benzyl-1H-benzimidazol-2-yl)-2-methylpropyl]-4-chlorobenzamide;
N-(3-aminopropyl)-N-[(1R)-1-(1-benzyl-1H-benzimidazol-2-yl)-2-methylpropyl]-4-methylbenzamide;
N-(3-aminopropyl)-N-[(1R)-1-(1-benzyl-5-methyl-1H-benzimidazol-2-yl)-2-methylpropyl]-4-methylbenzamide;
N-(3-aminopropyl)-N-[(1R)-1-(1-benzyl-5-chloro-1H-benzimidazol-2-yl)-2-methylpropyl]-4-methylbenzamide;
N-(3-aminopropyl)-N-{(1R)-1-[1-(4-chlorobenzyl)-6-fluoro-1H-benzimidazol-2-yl]-2-methylpropyl}-4-methylbenzamide;
N-(3-aminopropyl)-N-[(1R)-1-(1-benzyl-5-chloro-1H-benzimidazol-2-yl)propyl]-4-methylbenzamide;
N-(3-aminopropyl)-N-[(1R)-1-(1-benzyl-1H-benzimidazol-2-yl)-2-methylpropyl]-4-bromobenzamide;
N-(3-aminopropyl)-N-[(1R)-1-(1-benzyl-5-bromo-1H-benzimidazol-2-yl)-2-methylpropyl]-4-methylbenzamide;
N-(3-aminopropyl)-N-[(1R)-1-(1-benzyl-5-bromo-1H-benzimidazol-2-yl)propyl]benzamide;
N-(3-aminopropyl)-N-[(1R)-1-(1-benzyl-5-bromo-1H-benzimidazol-2-yl)propyl]-4-methylbenzamide;
N-(3-aminopropyl)-N-{(1R)-1-[1-(3-hydroxybenzyl)-5-methyl-1H-benzimidazol-2-yl]-2-methylpropyl}-4-methylbenzamide;
N-(3-aminopropyl)-N-{(1R)-1-[1-(3-fluorobenzyl)-5-methyl-1H-benzimidazol-2-yl]-2-methylpropyl}-4-methylbenzamide;
N-(3-aminopropyl)-N-[(1R)-1-(1-benzyl-5-ethyl-1H-benzimidazol-2-yl)-2-methylpropyl]-4-methylbenzamide;
N-(3-aminopropyl)-N-{(1R)-1-[5-ethyl-1-(3-hydroxybenzyl)-1H-benzimidazol-2-yl]-2-methylpropyl}-4-methylbenzamide;
N-(3-aminopropyl)-N-{(1R)-1-[5-ethyl-1-(3-fluorobenzyl)-1H-benzimidazol-2-yl]-2-methylpropyl}-4-methylbenzamide;
N-1-[(1R)-1-(1-benzyl-5-bromo-1H-benzimidazol-2-yl)-2-methylpropyl]-N-1-(4-methylbenzyl)-beta-alaninamide;
N-(3-aminopropyl)-N-[(1R)-1-(1-benzyl-5-vinyl-1H-benzimidazol-2-yl)-2-methylpropyl]-4-methylbenzamide;
N-(3-aminopropyl)-N-[(1R)-1-(1-benzyl-5-methoxy-1H-benzimidazol-2-yl)-2-methylpropyl]-4-methylbenzamide;
N-(3-aminopropyl)-N-[(1R)-1-(1-benzyl-5-phenyl-1H-benzimidazol-2-yl)-2-methylpropyl]-4-methylbenzamide;
2-(beta-alanylamino)-N-[(1R)-1-(1-benzyl-5-bromo-1H-benzimidazol-2-yl)-2-methylpropyl]-4-methylbenzamide;
(3R,5R)-5-[1-(3-hydroxybenzyl)-5-methyl-1H-benzimidazol-2-yl]-1-(4-methylbenzoyl)pyrrolidin-3-ol;
N-(3-aminopropyl)-N-[(1R)-1-(1-benzyl-5-ethynyl-1H-benzimidazol-2-yl)-2-methylpropyl]-4-methylbenzamide;
2-(2-aminoethyl)-3-[(1R)-1-(1-benzyl-5-bromo-1H-benzimidazol-2-yl)-2-methylpropyl]-7-methylquinazolin-4(3H)-one;
N-(3-aminopropyl)-3-fluoro-N-{(1R)-1-[1-(3-fluorobenzyl)-5-methyl-1H-benzimidazol-2-yl]-2-methylpropyl}-4-methylbenzamide;
N-(3-aminopropyl)-N-{(1R)-1-[1-(3-fluorobenzyl)-5-methyl-1H-benzimidazol-2-yl]-2-methylpropyl}benzamide;
N-(3-aminopropyl)-2,4-difluoro-N-{(1R)-1-[1-(3-fluorobenzyl)-5-methyl-1H-benzimidazol-2-yl]-2-methylpropyl}benzamide;
N-(3-aminopropyl)-N-{(1R)-1-[1-(3-fluorobenzyl)-5-methyl-1H-benzimidazol-2-yl]-2-methylpropyl}-3,4-dimethylbenzamide;
N-((1R)-1-{1-[3-(acetylamino)benzyl]-5-bromo-1H-benzimidazol-2-yl}-2-methylpropyl)-N-(3-aminopropyl)-4-methylbenzamide;
N-(3-aminopropyl)-2,6-difluoro-N-{(1R)-1-[1-(3-fluorobenzyl)-5-methyl-1H-benzimidazol-2-yl]-2-methylpropyl}benzamide;
N-(3-aminopropyl)-2-fluoro-N-{(1R)-1-[1-(3-fluorobenzyl)-5-methyl-1H-benzimidazol-2-yl]-2-methylpropyl}benzamide;
N-(3-aminopropyl)-N-{(1R)-1-[5-bromo-1-(3-chlorobenzyl)-1H-benzimidazol-2-yl]-2-methylpropyl}benzamide;
N-(3-aminopropyl)-N-{(1R)-1-[1-(3-fluorobenzyl)-5-methyl-1H-benzimidazol-2-yl]-2-methylpropyl}-4-nitrobenzamide;
N-(3-aminopropyl)-N-{(1R)-1-[1-(3-fluorobenzyl)-5-methyl-1H-benzimidazol-2-yl]-2-methylpropyl}nicotinamide;
N-(3-aminopropyl)-N-{(1R)-1-[1-(3-fluorobenzyl)-5-methyl-1H-benzimidazol-2-yl]-2-methylpropyl}isonicotinamide;
N-(3-aminopropyl)-N-{(1R)-1-[1-(3-fluorobenzyl)-5-methyl-1H-benzimidazol-2-yl]-2-methylpropyl}-2-naphthamide;
N-(3-aminopropyl)-N-{(1R)-1-[1-(3-fluorobenzyl)-5-methyl-1H-benzimidazol-2-yl]-2,2-dimethylpropyl}benzamide;
N-(3-aminopropyl)-N-{(1R)-1-[1-(3-fluorobenzyl)-5-methyl-1H-benzimidazol-2-yl]-2-methylpropyl}-4-hydroxybenzamide;
N-[3-(benzylamino)propyl]-N-[(1R)-1-(1-benzyl-5-chloro-1H-benzimidazol-2-yl)-2-methylpropyl]-4-methylbenzamide;
N-[(1R)-1-(1-benzyl-5-chloro-1H-benzimidazol-2-yl)-2-methylpropyl]-N-{3-[(cyclohexylmethyl)amino]propyl}-4-methylbenzamide;
N-(3-aminopropyl)-N-[(1R)-1-(1-benzyl-1H-benzimidazol-2-yl)-2,2-dimethylpropyl]benzamide;

N-[(1R)-1-(1-benzyl-5-chloro-1H-benzimidazol-2-yl)-2-methylpropyl]-N-[3-(isopropylamino)propyl]-4-methylbenzamide;

N-[(1R)-1-(1-benzyl-5-chloro-1H-benzimidazol-2-yl)-2-methylpropyl]-N-[3-(diethylamino)propyl]-4-methylbenzamide;

N-[(1R)-1-(1-benzyl-5-chloro-1H-benzimidazol-2-yl)-2-methylpropyl]-N-[3-(cyclobutylamino)propyl]-4-methylbenzamide;

N-(3-aminopropyl)-N-{(1R)-1-[5-bromo-1-(3,5-difluorobenzyl)-1H-benzimidazol-2-yl]-2-methylpropyl}benzamide;

N-(3-aminopropyl)-N-[1-(1-benzyl-5-chloro-1H-indol-2-yl)-2-methylpropyl]benzamide;

N-(3-aminopropyl)-N-[1-(1-benzyl-5-chloro-1H-indol-2-yl)-2-methylpropyl]-4-methylbenzamide;

N-(3-aminopropyl)-N-{1-[5-chloro-1-(phenylsulfonyl)-1H-indol-2-yl]-2-methylpropyl}-4-methylbenzamide;

N-{3-[(aminocarbonyl)(cyano)amino]propyl}-N-[(1R)-1-(1-benzyl-5-chloro-1H-benzimidazol-2-yl)-2-methylpropyl]-4-methylbenzamide;

N-{3-[(aminocarbonyl)amino]propyl}-N-[(1R)-1-(1-benzyl-5-chloro-1H-benzimidazol-2-yl)-2-methylpropyl]-4-methylbenzamide; and N-{(1R)-1-[1-(3-fluorobenzyl)-5-methyl-1H-benzimidazol-2-yl]-2-methylpropyl}-N-(1H-imidazol-4-ylmethyl)benzamide;

or a pharmaceutically acceptable salt or ester thereof.

20. A pharmaceutical composition comprising a therapeutically effective amount of a compound of claim 1 and a pharmaceutically acceptable carrier.

21. The composition of claim 20 further comprising at least one additional agent for the treatment of cancer.

22. The composition of claim 21, wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

* * * * *

UNITED STATES PATENT AND TRADEMARK OFFICE
CERTIFICATE OF CORRECTION

| | | |
|---|---|---|
| PATENT NO. | : 7,608,723 B2 | Page 1 of 1 |
| APPLICATION NO. | : 11/251440 | |
| DATED | : October 27, 2009 | |
| INVENTOR(S) | : Boyce et al. | |

It is certified that error appears in the above-identified patent and that said Letters Patent is hereby corrected as shown below:

On the Title page,

[*] Notice:   Subject to any disclaimer, the term of this patent is extended or adjusted under 35 U.S.C. 154(b) by 378 days.

Delete the phrase "by 378 days" and insert -- by 624 days --

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,608,723 B2
APPLICATION NO. : 11/251440
DATED : October 27, 2009
INVENTOR(S) : Boyce et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 870 days.

Signed and Sealed this

Twelfth Day of October, 2010

David J. Kappos
*Director of the United States Patent and Trademark Office*